United States Patent [19]

Lang

[11] Patent Number: 4,616,007
[45] Date of Patent: Oct. 7, 1986

[54] HETEROCYCLTHIO COMPOUNDS, PROCESS FOR THEIR MANUFACTURE, PHARMACEUTICAL PREPARATIONS THAT CONTAIN THESE COMPOUNDS, AND THE THE USE OF THE LATTER

[75] Inventor: Marc Lang, Rixheim, France

[73] Assignee: Ciba-Geigy Corporation, Ardsley, N.Y.

[21] Appl. No.: 755,225

[22] Filed: Jul. 15, 1985

Related U.S. Application Data

[63] Continuation of Ser. No. 549,142, Nov. 7, 1983, abandoned.

[30] Foreign Application Priority Data

Nov. 16, 1982 [CH] Switzerland ............... 6671/82

[51] Int. Cl.$^4$ ............... C07D 205/08; C07D 513/04; A61K 31/425
[52] U.S. Cl. ............... 514/192; 514/195; 546/270; 540/310; 540/357
[58] Field of Search ............... 260/245.2 R; 514/210, 514/195, 192; 546/270

[56] References Cited

U.S. PATENT DOCUMENTS 4,272,437 6/1981 Menard et al. ............... 260/239 A

FOREIGN PATENT DOCUMENTS

| 2210 | 6/1979 | European Pat. Off. . |
| 3960 | 9/1979 | European Pat. Off. . |
| 69373 | 5/1983 | European Pat. Off. . |
| 3224055 | 1/1983 | Fed. Rep. of Germany . |
| 2043639 | 10/1980 | United Kingdom . |

OTHER PUBLICATIONS

Japanese Patent Publication 57,179,190 (Abstract) (Apr. 1982).

*Primary Examiner*—Mark L. Berch
*Attorney, Agent, or Firm*—Michael W. Glynn; Irving M. Fishman

[57] ABSTRACT

2-heterocyclythio-lower alkyl-2-penem compounds of the formula

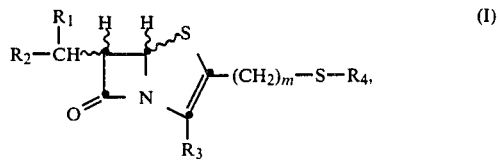

in which $R_1$ represents hydrogen or methyl, $R_2$ represents an optionally protected hydroxy group, $R_3$ represents carboxy or protected carboxy $R_3'$, $R_4$ represents an unsaturated monocyclic heterocyclyl radical that is bonded via a ring carbon atom to the sulphur atom, and m is 2, 3 or 4, and salts of such compounds of the formula I that have a salt-forming group, optical isomers of compounds of the formula I and mixtures of these optical isomers, possess antibiotic properties. The compounds are manufactured according to processes known per se.

9 Claims, No Drawings

HETEROCYCLTHIO COMPOUNDS, PROCESS FOR THEIR MANUFACTURE, PHARMACEUTICAL PREPARATIONS THAT CONTAIN THESE COMPOUNDS, AND THE THE USE OF THE LATTER

This application is a continuation of application Ser. No. 549,142, filed Nov. 7, 1983 now abandoned.

The present invention relates to novel 2-heterocyclylthio-lower alkylpenem compounds, to processes for their manufacture, to pharmaceutical preparations that contain such compounds, and to their use for the manufacture of pharmaceutical preparations or as pharmacologically active compounds.

The invention relates especially to 2-heterocyclylthio-lower alkyl-2-penem compounds of the formula

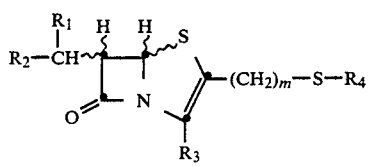

in which
$R_1$ represents hydrogen or methyl,
$R_2$ represents an optionally protected hydroxy group,
$R_3$ represents carboxy or protected carboxy $R_3'$,
$R_4$ represents an unsaturated monocyclic heterocyclyl radical that is bonded via a ring carbon atom to the sulphur atom and m is 2, 3 or 4, and to salts of such compounds of the formula I that have a salt-forming group, to optical isomers of compounds of the formula I and mixtures of these optical isomers, to processes for the manufacture of compounds of the formula I, to pharmaceutical preparations containing such compounds, and to their use for the manufacture of pharmaceutical preparations or as pharmacologically active compounds.

Within the scope of the present description, the definitions used hereinbefore and hereinafter have preferably the following meanings:

An unsaturated monocyclic heterocyclyl radical $R_4$ that is bonded via a ring carbon atom to the sulphur atom is especially a corresponding 5-membered or 6-membered heteroaryl radical or partially saturated heteroaryl radical having from 1 to 4 ring nitrogen atoms and optionally an additional ring hetero atom from the group comprising oxygen and sulphur, such as a corresponding 5-membered aza-, diaza-, triaza-, tetraza-, oxaza-, oxadiaza-, thiaza-, thiadiaza- or thiatriazacyclic radical of aromatic character or a corresponding dihydro radical, or a corresponding 6-membered aza-, diaza- or triaza-cyclic radical of aromatic character, and a corresponding dihydro or tetrahydro radical. These radicals are unsubstituted or may be substituted, such as mono- or poly-substituted, such as, especially, disubstituted, by optionally etherified or esterified, including protected, hydroxy, for example hydroxy, lower alkoxy, lower alkanoyloxy or halogen, optionally etherified mercapto, for example mercapto, lower alkylthio or phenylthio, lower alkyl, hydroxy-lower alkyl, lower alkoxy-lower alkyl, carboxy-lower alkyl, optionally N-lower alkylated amino-lower alkyl, for example amino-lower alkyl or di-lower alkylamino-lower alkyl, sulpho-lower alkyl, optionally substituted, including protected, amino, for example amino, lower alkylamino, di-lower alkylamino, lower alkyleneamino or acylamino, such as lower alkanoylamino, optionally functionally modified, including protected, carboxy or sulpho, for example carboxy, esterified carboxy, such as lower alkoxycarbonyl, optionally substituted carbamoyl, such as N-mono- or N,N-di-lower alkylated carbamoyl, cyano, sulpho or sulphamoyl, phenyl optionally substituted by lower alkyl, nitro, lower alkoxy and/or by halogen, cycloalkyl, nitro, oxo and/or oxido.

In the present description, the term "lower" used in connection with definitions of groups or compounds denotes that, unless expressly defined otherwise, the groups and compounds so designated contain up to and including 7, preferably up to and including 4, carbon atoms.

Lower alkoxy is, for example, methoxy, also ethoxy, n-propoxy, isopropoxy, n-butoxy, isobutoxy or tert.-butoxy, and also n-pentyloxy, n-hexyloxy or n-heptyloxy.

Lower alkanoyloxy is, for example, acetoxy or propionyloxy.

Halogen is, for example, fluorine, chlorine, bromine or iodine.

Lower alkylthio is, for example, methylthio, ethylthio, n-propylthio, isopropylthio or n-butylthio.

Lower alkyl is, for example, methyl, ethyl, n-propyl, isopropyl, n-butyl, isobutyl, sec.-butyl or tert.-butyl, and also n-pentyl, n-hexyl or n-heptyl.

Hydroxy-lower alkyl is, for example, hydroxymethyl, 2-hydroxyethyl or 2,3-dihydroxypropyl.

Lower alkoxy-lower alkyl is, for example, methoxymethyl, 2-methoxyethyl, ethoxymethyl or 2-ethoxyethyl.

Carboxy-lower alkyl is, for example, carboxymethyl, 1-carboxy-, 2-carboxy- or 1,2-dicarboxy-ethyl.

Amino-lower alkyl is, for example, aminomethyl or 2-aminoethyl, whilst di-lower alkylamino-lower alkyl is, for example, dimethylaminomethyl, 2-dimethylaminoethyl or 2-diethylaminoethyl.

Sulpho-lower alkyl is, for example, sulphomethyl or 2-sulphoethyl.

Lower alkylamino is, for example, methylamino, ethylamino, n-propylamino, isopropylamino or n-butylamino, whilst di-lower alkylamino is, for example, dimethylamino, diethylamino, di-n-propylamino or diisopropylamino.

Lower alkyleneamino has especially from 4 to 6 carbon chain members and represents, for example, pyrrolidino or piperidino.

Lower alkanoylamino is, for example, acetylamino or propionylamino.

Lower alkoxycarbonyl is, for example, methoxycarbonyl or ethoxycarbonyl.

N-mono-lower alkylated carbamoyl is, for example, N-methyl-, N-ethyl- or N-propyl-carbamoyl, whilst N,N-di-lower alkylated carbamoyl represents, for example, N,N-dimethyl- or N,N-diethyl-carbamoyl.

Cycloalkyl contains preferably from 3 to 8, especially 5 or 6, ring members and is, for example, cyclopentyl or cyclohexyl, and also cyclopropyl and cycloheptyl.

Corresponding 5-membered optionally partially saturated heteroaryl radicals $R_4$ are, for example, pyrrolyl or dihydropyrrolyl optionally substituted by lower alkyl, for example 1-methyl-2-pyrrolyl or 4,5-dihydro-3-pyrrolyl; diazolyl, such as imidazolyl, optionally substituted by lower alkyl, for example 2-imidazolyl; triazolyl, such as 1H-1,2,3-triazol-4-yl, 1H-1,2,4-triazol-3-yl or 4H-1,2,4-triazol-3-yl, optionally substituted by lower alkyl, carboxy-lower alkyl or by phenyl, for example the corresponding unsubstituted radicals, and also 1-methyl-1H-1,2,3-triazol-4-yl, 5-methyl-1H-1,2,4-triazol-3-yl, 3-methyl-1-phenyl-1H-1,2,4-triazol-5-yl, 4,5-dimethyl-, 4-carboxymethyl- or 4-phenyl-4H-1,2,4-triazol-3-yl; tetrazolyl, such as 1H- or 2H-tetrazol-5-yl, optionally substituted by lower alkyl, carboxylower alkyl, sulpho-lower alkyl, di-lower alkylaminolower alkyl or by phenyl which optionally contains substituents, such as halogen, for example 1H-tetrazol-5-yl, 1-methyl-1H-tetrazol-5-yl, 1-carboxymethyl-1H-tetrazol-5-yl, 1-(2-carboxyethyl)-1H-tetrazol-5-yl, 1-sulphomethyl-1H-tetrazol-5-yl, 1-(2-sulphoethyl)-1H-tetrazol-5-yl, 1-(2-dimethylaminoethyl)-1H-tetrazol-5-yl, 1-phenyl-1H-tetrazol-5-yl or 2-methyl-2H-tetrazol-5-yl; thiazolyl, such as 2-thiazolyl, or isothiazolyl, such as 3-isothiazolyl, optionally substituted by lower alkyl or amino, for example 2-thiazolyl, 4,5-dimethyl-2-thiazolyl or 3-isothiazolyl; thiadiazolyl, such as 1,2,3-thiadiazol-4-yl, 1,2,3-thiadiazol-5-yl, 1,3,4-thiadiazol-2-yl or 1,2,4-thiadiazol-5-yl, optionally substituted by lower alkyl or amino, for example the corresponding unsubstituted groups, and also 2-methyl-1,3,4-thiadiazol-5-yl, 2-amino-1,3,4-thiadiazol-5-yl or 3-methyl-1,2,4-thiadiazol-5-yl; thiatriazolyl, for example 1,2,3,4-thiatriazol-5-yl; oxazolyl or isoxazolyl, such as 2-oxazolyl or 5-isoxazolyl, optionally substituted by lower alkyl and/or phenyl, for example the corresponding unsubstituted radicals, and also 4-methyl-5-oxazolyl, 4,5-diphenyl-2-oxazolyl or 3-methyl-5-isoxazolyl; or oxadiazolyl, such as 1,2,4-oxadiazol-5-yl or 1,3,4-oxadiazol-2-yl, optionally substituted by lower alkyl or by optionally nitro-substituted phenyl, for example the corresponding unsubstituted groups, and also 2-methyl-1,3,4-oxadiazol-5-yl, 2-phenyl-1,3,4-oxadiazol-5-yl or 2-(4-nitrophenyl)-1,3,4-oxadiazol-5-yl.

Corresponding 6-membered optionally partially saturated heteroaryl radicals $R_4$ are, for example, pyridyl, such as 2-, 3- or 4-pyridyl, optionally substituted by halogen and/or oxido, for example 2-pyridyl, 4-pyridyl, 1-oxido-2-pyridyl or 4-chloro-1-oxido-2-pyridyl; pyridazinyl, such as 6-pyridazinyl, optionally substituted by lower alkyl, hydroxy, lower alkoxy, halogen and/or by oxido, for example 3-hydroxy-6-pyridazinyl, 2-oxido-6-pyridazinyl, 3-chloro-1-oxido-6-pyridazinyl, 3-methyl-2-oxido-6-pyridazinyl, 3-methoxy-1-oxido-6-pyridazinyl or 3-ethoxy-1-oxido-6-pyridazinyl; 1,2-dihydropyrimidinyl, such as 1,2-dihydro-4-pyrimidinyl, optionally substituted by lower alkyl, amino, di-lower alkylamino, oxo and/or by carboxy, for example 2-oxo-1,2-dihydro-4-pyrimidinyl, 6-methyl-, 5-methyl-, 6-amino-, 6-dimethylamino-, 5-carboxy- or 6-carboxy-2-oxo-1,2-dihydro-4-pyrimidinyl; or partially saturated triazinyl, such as tetrahydro-1,2,4-triazin-3-yl, optionally substituted by lower alkyl and/or by up to two oxo groups, especially N-lower alkyl-5,6-dioxo-1,4,5,6-tetrahydro-1,2,4-triazin-3-yl, for example 1- or 4-methyl-5,6-dioxo-1,4,5,6-tetrahydro-1,2,4-triazin-3-yl.

The functional groups present in compounds of the formula I, such as hydroxy, carboxy, amino or sulpho groups, especially the hydroxy group $R_2$ and the carboxy group $R_3$, are optionally protected by protecting groups used in penem, penicillin, cephalosporin and peptide chemistry.

Such protecting groups can be removed readily, that is to say without undesirable secondary reactions taking place, for example by solvolysis or reduction, or alternatively under physiological conditions.

Protecting groups of this type and the methods by which they are introduced and removed are described, for example, in J. F. W. McOmie, "Protective Groups in Organic Chemistry", Plenum Press, London, New York, 1973;

T. W. Greene, "Protective Groups in Organic Synthesis", Wiley, New York, 1981;

"The Peptides", Vol. I, Schroeder and Luebke, Academic Press, London, New York, 1965, and in Houben-Weyl, "Methoden der Organischen Chemie", Vol. 15/1, Georg Thieme Verlag, Stuttgart, 1974.

In compounds of the formula (I), a hydroxy group $R_2$ and also a hydroxy group present in the radical $R_4$ may be protected, for example, by acyl radicals. Suitable acyl radicals are, for example, lower alkanoyl optionally substituted by halogen, for example acetyl or trifluoroacetyl, benzoyl optionally substituted by nitro, for example benzoyl, 4-nitrobenzoyl or 2,4-dinitrobenzoyl, lower alkoxycarbonyl optionally substituted by halogen, for example 2-bromoethoxycarbonyl or 2,2,2-trichloroethoxycarbonyl, or phenyllower alkoxycarbonyl optionally substituted by nitro, for example 4-nitrobenzyloxycarbonyl. Further suitable hydroxy-protecting groups are, for example, trisubstituted silyl, such as tri-lower alkylsilyl, for example trimethylsilyl or tert.-butyl-dimethyl-silyl, 2-halo-lower alkyl groups, for example 2-chloro-, 2-bromo-, 2-iodo- and 2,2,2-trichloroethyl, and phenyl-lower alkyl optionally substituted by halogen, for example chlorine, lower alkoxy, for example methoxy, and/or by nitro, such as corresponding benzyl. Tri-lower alkylsilyl is preferred as hydroxy-protecting group.

A carboxy group $R_3$ and also a carboxy group present in the radical $R_4$ is customarily protected in esterified form, the ester group being readily cleavable under mild conditions, for example under mildly reductive, such as hydrogenolytic, conditions, or under mildly solvolytic, such as acidolytic, or especially basic or neutral hydrolytic, conditions. A protected carboxy group can also be an esterified carboxy group that can be cleaved under physiological conditions or readily converted into a different functionally modified carboxy group, such as into a different esterified carboxy group.

Such esterified carboxy groups contain as esterifying groups especially lower alkyl groups that are branched in the 1-position or suitably substituted in the 1- or 2-position. Preferred carboxy groups in esterified form are, inter alia, lower alkoxycarbonyl, for example methoxycarbonyl, ethoxycarbonyl, isopropoxycarbonyl or tert.-butoxycarbonyl, and (hetero)arylmethoxycarbonyl having from 1 to 3 aryl radicals or having a monocyclic heteroaryl radical, these optionally being mono- or poly-substituted, for example by lower alkyl, such as tert.-lower alkyl, for example tert.-butyl, halogen, for example chlorine, and/or by nitro. Examples of such groups are benzyloxycarbonyl optionally substituted, for example, as mentioned above, for example 4-nitrobenzyloxycarbonyl, diphenylmethoxycarbonyl or triphenylmethoxycarbonyl optionally substituted, for example, as mentioned above, for example diphenylmethoxycarbonyl, or picolyloxycarbonyl, for example 4-picolyloxycarbonyl, or furfuryloxycarbonyl, such as 2-furfuryloxycarbonyl, optionally substituted, for example, as mentioned above. Further suitable groups are lower alkanoylmethoxycarbonyl, such as acetonyloxycarbonyl, aroylmethoxycarbonyl, in which the aroyl group preferably represents benzoyl optionally substituted, for example, by halogen, such as bromine, for example phenacyloxycarbonyl, halo-lower alkoxycarbonyl, such as 2-halo-lower alkoxycarbonyl, for example 2,2,2-trichloroethoxycarbonyl, 2-chloroethoxycarbonyl, 2-bromoethoxycarbonyl or 2-iodoethoxycarbonyl, or ω-halolower alkoxycarbonyl in which lower alkoxy contains from 4 to 7 carbon atoms, for example 4-chlorobutoxycarbonyl, phthalimidomethoxycarbonyl, lower alkenyloxycarbonyl, for example allyloxycarbonyl, or ethoxycarbonyl substituted in the 2-position by lower alkylsulphonyl, cyano or by tri-substituted silyl, such as tri-lower alkylsilyl or triphenylsilyl, for example 2-methylsulphonylethoxycarbonyl, 2-cyanoethoxycarbonyl, 2-trimethylsilylethoxycarbonyl or 2-(di-n-butyl-methylsilyl)-ethoxycarbonyl.

Other protected carboxy groups in esterified form are corresponding organic silyloxycarbonyl groups, and also corresponding organic stannyloxycarbonyl groups. In these groups the silicon or tin atom preferably has tri-lower alkyl, especially methyl or ethyl, and also lower alkoxy, for example methoxy, as substituents. Suitable silyl and stannyl groups are especially tri-lower alkylsilyl, especially trimethylsilyl or dimethyl-tert.-butylsilyl, or correspondingly substituted stannyl groups, for example tri-n-butylstannyl.

An esterified carboxy group that can be cleaved under physiological conditions is especially an acyloxymethoxycarbonyl group in which acyl represents, for example, the radical of an organic carboxylic acid, especially of an optionally substituted lower alkanecarboxylic acid, or in which acyloxymethyl forms the radical of a lactone, 1-lower alkoxy-lower alkoxycarbonyl or alternatively 1-lower alkoxycarbonyloxy-lower alkoxycarbonyl in which lower alkyl represents, for example, methyl, propyl, butyl or especially ethyl, and lower alkoxy represents, for example, methoxy, ethoxy, propoxy or butoxy. Such groups are, for example, lower alkanoyloxymethoxycarbonyl, for example acetoxymethoxycarbonyl or pivaloyloxymethoxycarbonyl, amino-lower alkanoyloxymethoxycarbonyl, especially α-amino-lower alkanoyloxymethoxycarbonyl, for example glycyloxymethoxycarbonyl, L-valyloxymethoxycarbonyl, L-leucyloxymethoxycarbonyl, phthalidyloxycarbonyl, 4-crotonolactonyl or 4-butyrolacton-4-yl, indanyloxycarbonyl, for example 5-indanyloxycarbonyl, 1-ethoxycarbonyloxyethoxycarbonyl, methoxymethoxycarbonyl or 1-methoxyethoxycarbonyl.

Preferred protected carboxy groups $R_3'$ are the 4-nitrobenzyloxycarbonyl and lower alkenyloxycarbonyl groups and the ethoxycarbonyl group substituted in the 2-position by lower alkylsulphonyl, cyano or tri-lower alkylsilyl, and esterified carboxy groups that can be cleaved under physiological conditions, such as lower alkanoyloxymethoxycarbonyl and 1-lower alkoxycarbonyloxy-lower alkoxycarbonyl.

A protected amino group can be, for example, in the form of a readily cleavable acylamino, acylimino, etherified mercaptoamino, silylamino or stannylamino group or in the form of an enamino, nitro or azido group.

In a corresponding acylamino group, acyl is, for example, the acyl radical of an organic acid having, for example, up to 18 carbon atoms, especially an alkanecarboxylic acid optionally substituted, for example, by halogen or phenyl, or a benzoic acid optionally substituted, for example, by halogen, lower alkoxy or nitro, or of a carbonic acid semiester. Such acyl groups are, for example, lower alkanoyl, such as formyl, acetyl or propionyl, halo-lower alkanoyl, such as 2-haloacetyl, especially 2-fluoro-, 2-bromo-, 2-iodo-, 2,2,2-trifluoro- or 2,2,2-trichloro-acetyl, optionally substituted benzoyl, for example benzoyl, halobenzoyl, such as 4-chlorobenzoyl, lower alkoxybenzoyl, such as 4-methoxybenzoyl, or nitrobenzoyl, such as 4-nitrobenzoyl. Especially suitable are also lower alkenyloxycarbonyl, for example allyloxycarbonyl, or lower alkoxycarbonyl optionally substituted in the 1- or 2-position, such as lower alkoxycarbonyl, for example methoxy- or ethoxy-carbonyl, optionally substituted benzyloxycarbonyl, for example benzyloxycarbonyl or 4-nitrobenzyloxycarbonyl, aroylmethoxycarbonyl in which the aroyl group preferably represents benzoyl optionally substituted, for example, by halogen, such as bromine, for example phenacyloxycarbonyl, 2-halo-lower alkoxycarbonyl, for example 2,2,2-trichloroethoxycarbonyl, 2-chloroethoxycarbonyl, 2-bromoethoxycarbonyl or 2-iodoethoxycarbonyl, or 2-(trisubstituted silyl)-ethoxycarbonyl, such as 2-tri-lower alkylsilylethoxycarbonyl, for example 2-trimethylsilylethoxycarbonyl or 2-(di-n-butyl-methylsilyl)-ethoxycarbonyl, or 2-triarylsilylethoxycarbonyl, such as 2-triphenylsilylethoxycarbonyl.

In an acylimino group, acyl is, for example, the acyl radical of an organic dicarboxylic acid having, for example, up to 12 carbon atoms, especially a corresponding aromatic dicarboxylic acid, such as phthalic acid. Such a group is especially phthalimino.

An etherified mercaptoamino group is especially a phenylthioamino group optionally substituted by lower alkyl, such as methyl or tert.-butyl, lower alkoxy, such as methoxy, halogen, such as chlorine or bromine, and/or by nitro, or a pyridylthioamino group. Corresponding groups are, for example, 2- or 4-nitrophenylthioamino or 2-pyridylthioamino.

A silyl- or stannyl-amino group is especially an organic silyl- or stannyl-amino group in which the silicon or tin atom preferably has substituent(s) selected from lower alkyl, for example methyl, ethyl, n-butyl or tert.-butyl, also lower alkoxy, for example methoxy. Corresponding silyl or stannyl groups are especially tri-lower alkylsilyl, especially trimethylsilyl, also dimethyl-tert.-butyl-silyl, or correspondingly substituted stannyl, for example tri-n-butylstannyl.

Further protected amino groups are, for example, enamino groups that contain an electron-attracting substituent, for example a carbonyl group, at the double bond in the 2-position. Protecting groups of this type are, for example, 1-acyl-lower alk-1-en-2-yl radicals in which acyl represents, for example, the corresponding radical of a lower alkanecarboxylic acid, for example acetic acid, a benzoic acid optionally substituted, for example, by lower alkyl, such as methyl or tert.-butyl, lower alkoxy, such as methoxy, halogen, such as chlorine, and/or by nitro, or especially of a carbonic acid semiester, such as a carbonic acid-lower alkyl semiester, for example a carbonic acid methyl semiester or ethyl semiester, and in which lower alk-1-ene represents especially 1-propene. Corresponding protecting groups are especially 1-lower alkanoylprop-1-en-2-yl, for example 1-acetylprop-1-en-2-yl, or 1-lower alkoxycarbonylprop-1-en-2-yl, for example 1-ethoxycarbonylprop-1-en-2-yl.

A protected sulpho group is especially an esterified sulpho group, such as a sulpho group esterified by an aliphatic, cycloaliphatic, cycloaliphatic-aliphatic, aromatic or araliphatic alcohol, for example a lower alkanol, or by a silyl or stannyl radical, such as tri-lower alkylsilyl. In a sulpho group the hydroxy group may be etherified, for example in the same manner as the hydroxy group in an esterified carboxy group.

Salts of compounds according to the invention are especially pharmaceutically acceptable, non-toxic salts of compounds of the formula I. Such salts are formed, for example, from the acidic groups present in compounds of the formula I, for example carboxy and sulpho groups, and are especially metal or ammonium salts, such as alkali metal and alkaline earth metal salts, for example sodium, potassium, magnesium or calcium salts, and ammonium salts with ammonia or suitable organic amines, such as lower alkylamines, for example triethylamine, hydroxy-lower alkylamines, for example 2-hydroxyethylamine, bis-(2-hydroxyethyl)-amine or tris-(2-hydroxyethyl)-amine, basic aliphatic esters of carboxylic acids, for example 4-aminobenzoic acid 2-diethylaminoethyl ester, lower alkyleneamines, for example 1-ethylpiperidine, cycloalkylamines, for example dicyclohexylamine, or benzylamines, for example N,N'-dibenzylethylenediamine, dibenzylamine or N-benzyl-β-phenethylamine. Compounds of the formula I having a basic group, for example having an amino group, can form acid addition salts, for example with inorganic acids, such as hydrochloric acid, sulphuric acid or phosphoric acid, or with suitable organic carboxylic or sulphonic acids, for example acetic acid, succinic acid, fumaric acid, maleic acid, tartaric acid, oxalic acid, citric acid, benzoic acid, mandelic acid, malic acid, ascorbic acid, methanesulphonic acid or 4-toluenesulphonic acid. Compounds of the formula I having an acidic group and a basic group can also be in the form of internal salts, that is to say in zwitterionic form.

For the purposes of isolation or purification it is also possible to use pharmaceutically unacceptable salts. Only the pharmaceutically acceptable, non-toxic salts are used therapeutically, however, and these are therefore preferred.

In the penem compounds of the formula I, the two asymmetric carbon atoms in the 5- and 6-positions can be in the R-, the S- or the racemic R,S-configuration. The compounds in which the configuration of the 5-carbon atom corresponds to that of natural penicillin (5R-configuration) are preferred. The hydrogen atoms in 5- and 6-positions can be in the cis- or, preferably, in the trans-position with respect to one another. In the preferred configuration the substituent in the 6-position assumes the S-configuration. Compounds of the formula I in which $R_1$ is methyl have at the α-carbon atom of the side chain (carbon atom 8), a further chirality centre which can be in the S-configuration, the racemic R,S-configuration or, preferably, the R-configuration.

The invention relates especially to compounds of the formula I in which $R_1$ represents hydrogen or methyl, $R_2$ represents hydroxy or protected hydroxy, $R_3$ represents carboxy or protected carboxy $R_3'$, especially esterified carboxy that can be cleaved under physiological conditions, $R_4$ represents a monocyclic 5-membered or 6-membered heteroaryl radical or partially saturated heteroaryl radical that is bonded via a ring carbon atom to the sulphur atom and has from 1 to 4 ring nitrogen atoms and optionally an additional ring hetero atom from the group comprising oxygen and sulphur, such as a corresponding 5-membered aza-, diaza-, triaza-, tetraza-, oxaza-, oxadiaza-, thiaza-, thiadiaza- or thiatriaza-cyclic radical of aromatic character or a corresponding dihydro radical, or a corresponding 6-membered aza-, diaza- or triaza-cyclic radical of aromatic character, or a corresponding dihydro or tetrahydro radical, these radicals being unsubstituted or substituted by hydroxy, lower alkoxy, lower alkanoyloxy, halogen, mercapto, lower alkylthio, phenylthio, lower alkyl, hydroxy-lower alkyl, lower alkoxy-lower alkyl, carboxy-lower alkyl, amino-lower alkyl, di-lower alkylamino-lower alkyl, sulpho-lower alkyl, amino, lower alkylamino, di-lower alkylamino, lower alkyleneamino, lower alkanoylamino, carboxy, lower alkoxycarbonyl, optionally N-mono- or N,N-di-lower alkylated carbamoyl, cyano, sulpho, sulphamoyl, phenyl optionally substituted by lower alkyl, nitro, lower alkoxy and/or by halogen, cycloalkyl, nitro, oxo and/or oxido, and m representing 2, 3 or 4, and to salts of compounds of the formula I that have a salt-forming group, to optical isomers of compounds of the formula I and mixtures of these optical isomers.

The invention relates more especially to compounds of the formula I in which $R_1$ represents hydrogen or methyl, $R_2$ represents hydroxy, $R_3$ represents carboxy, lower alkanoyloxymethoxycarbonyl, for example pivaloyloxymethoxycarbonyl, or 1-lower alkoxycarbonyloxy-lower alkoxycarbonyl, for example 1-ethoxycarbonyloxyethoxycarbonyl, $R_4$ represents thiadiazolyl, such as 1,2,3-thiadiazol-4-yl, 1,2,3-thiadiazol-5-yl, 1,3,4-thiadiazol-2-yl or 1,2,4-thiadiazol-5-yl, optionally substituted by lower alkyl, for example 1,3,4-thiadiazol-2-yl or 2-methyl-1,3,4-thiadiazol-5-yl, oxadiazolyl, such as 1,2,4-oxadiazol-5-yl or 1,3,4-oxadiazol-2-yl, optionally substituted by lower alkyl, for example 2-methyl-1,3,4-oxadiazol-5-yl, tetrazolyl, such as 1H- or 2H-tetrazol-5-yl, optionally substituted by lower alkyl, carboxy-lower alkyl, sulpholower alkyl or di-lower alkylamino-lower alkyl, for example 1H-tetrazol-5-yl, 1-methyl-1H-tetrazol-5-yl, 1-carboxymethyl-1H-tetrazol-5-yl, 1-sulphomethyl-1H-tetrazol-5-yl, 1-(2-dimethylaminoethyl)-1H-tetrazol-5-yl or 2-methyl-2H-tetrazol-5-yl, or pyridyl, for example 2-pyridyl, each bonded via a ring carbon atom to the sulphur atom, and m represents 2 or 3, and to pharmaceutically acceptable salts of such compounds of the formula I that contain a salt-forming group, to optical isomers, for example the (5R,6S)-isomer, of compounds of the formula I and mixtures of these optical isomers.

The invention relates most especially to (5R,6S)-configured compounds of the formula I in which $R_1$ represents hydrogen, $R_2$ represents hydroxy, $R_3$ represents carboxy, $R_4$ represents tetrazol-5-yl substituted by lower alkyl or di-lower alkylamino-lower alkyl, for example 1-methyl-1H-tetrazol-5-yl or 1-(2-dimethylaminoethyl)-1H-tetrazol-5-yl and m represents 2 or 3, and to pharmaceutically acceptable salts of compounds of the formula I.

The invention relates above all to the compounds of the formula I mentioned in the Examples and the pharmaceutically acceptable salts thereof.

The compounds of the present invention are manufactured by processes known per se.

The novel compounds are manufactured, for example, as follows:

(a) an ylide compound of the formula

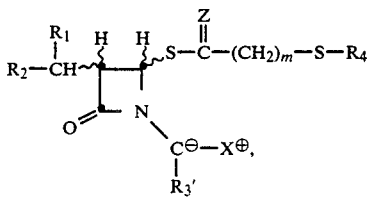

in which $R_1$, $R_2$, $R_3'$, $R_4$ and m have the meanings given under formula I, a hydroxy group $R_2$ and functional groups which may be present in the radical $R_4$ preferably being in protected form, Z represents oxygen or sulphur and $X^\oplus$ represents either a trisubstituted phosphonio group or a diesterified phosphono group together with a cation, is cyclised, or (b) a compound of the formula

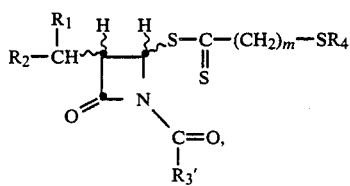

in which $R_1$, $R_2$, $R_3'$, $R_4$ and m have the meanings given under formula I, a hydroxy group $R_2$ and functional groups which may be present in the radical $R_4$ preferably being in protected form, is treated with an organic compound of trivalent phosphorous, or (c) a compound of the formula

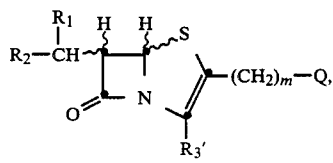

in which $R_1$, $R_2$, $R_3'$ and m have the meanings given under formula I and Q represents a radical which can be replaced by nucleophilic reaction, is treated with a mercaptan of the formula $R_4$—SH, and, if desired or necessary, in a resulting compound of the formula I a protected hydroxy group $R_2$ is converted into a free hydroxy group, and/or, if desired, in a resulting compound of the formula I a protected carboxy group $R_3'$ is converted into a free carboxy group or into a different protected carboxy group $R_3'$, and/or, if desired, other protected functional groups in the radical $R_4$ are converted into the free functional groups, and/or, if desired, in a resulting compound of the formula I a radical $R_4$ is converted into a different radical $R_4$, and/or, if desired, a resulting compound having a salt-forming group is converted into a salt, or a resulting salt is converted into the free compound or into a different salt, and/or, if desired, a resulting mixture of isomeric compounds is separated into the individual isomers.

(a) Cyclisation of the compound of the formula II

The group $X^\oplus$ in a starting material of the formula II is one of the phosphonio or phosphono groups customarily used in Wittig condensation reactions, especially a triaryl-, for example triphenyl-, or trilower alkyl-, for example tri-n-butyl-phosphonio group, or a phosphono group diesterified by lower alkyl, for example ethyl, the symbol $X^\oplus$ in the case of the phosphono group including in addition the cation of a strong base, especially a suitable metal ion, such as an alkali metal ion, for example a lithium, sodium or potassium ion. Preferred as the group $X^\oplus$ is, on the one hand, triphenylphosphonio and, on the other hand, diethylphosphono together with an alkali metal ion, for example a sodium ion.

The ylide compounds of the formula II are, in the isomeric ylene form, also termed phosphorane compounds. In phosphonio compounds of the formula II, the negative charge is neutralised by the positively charged phosphonio group. In phosphono compounds of the formula II, the negative charge is neutralised by the cation of a strong base, which, depending upon the method of manufacture of the phosphono starting material, may be, for example, an alkali metal ion, for example a sodium, lithium or potassium ion. The phosphono starting materials are therefore used as salts in the reaction.

Cyclisation may take place spontaneously, that is to say in the manufacture of the starting materials, or be effected by heating, for example in a temperature range of approximately from 30° to 160° C., preferably from approximately 50° to approximately 100° C. The reaction is preferably carried out in a suitable inert solvent, such as an aliphatic, cycloaliphatic or aromatic hydrocarbon, for example hexane, cyclohexane, benzene or toluene, a halogenated hydrocarbon, for example methylene chloride, an ether, for example diethyl ether, dimethoxyethane or diethylene glycol-dimethyl ether, a cyclic ether, for example dioxan or tetrahydrofuran, a carboxylic acid amide, for example dimethylformamide, a di-lower alkyl sulphoxide, for example dimethyl sulphoxide, or a lower alkanol, for example methanol, ethanol or tert.-butanol, or in a mixture thereof, and, if necessary, in an inert gas atmosphere, for example a nitrogen atmosphere.

A starting compound of the formula II in which $X^\oplus$ represents a phosphono group together with a cation is preferably manufactured in situ by treating a compound of the formula

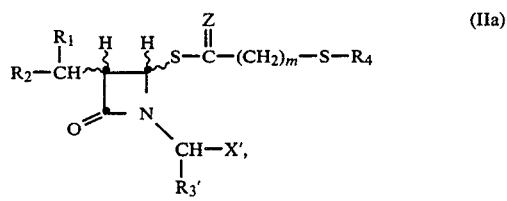

in which X' represents a phosphono group, with a suitable basic reagent, such as an inorganic base, for example an alkali metal carbonate, such as sodium or potassium carbonate, or an organic base, such as a tri-lower alkylamine, for example triethylamine, or a cyclic base of the amidine type, such as a corresponding diazabicycloalkene compound, for example 1,5-diazabicyclo[5.4.-0]undec-5-ene.

(b) Cyclisation of the compound of the formula III

An organic compound of trivalent phosphorus is derived, for example, from phosphorous acid and is especially an ester thereof with a lower alkanol, for example methanol or ethanol, and/or an optionally substituted aromatic hydroxy compound, for example phenol or pyrocatechol, or an amide ester thereof of the formula $P(OR_a)_2\text{-}N(R_b)_2$ in which each of $R_a$ and $R_b$, independently of the other, represents lower alkyl, for example methyl, or aryl, for example phenyl. Preferred compounds of trivalent phosphorus are tri-alkyl phosphites, for example trimethyl phosphite or triethyl phosphite.

The reaction is preferably carried out in an inert solvent, such as an aromatic hydrocarbon, for example benzene or toluene, an ether, for example dioxan or tetrahydrofuran, or a halogenated hydrocarbon, for example methylene chloride or chloroform, at a temperature of from approximately 20° to approximately 80° C., preferably at from approximately 40° to approximately 60° C., one molar equivalent of a compound of the formula III being reacted with two molar equivalents of the phosphorus compound. Preferably, the compound of the formula III is placed in an inert solvent and the phosphorus compound, preferably dissolved in the same inert solvent, is added dropwise over a prolonged period, for example over a period of from 2 to 4 hours.

The starting compounds of the formula III can be manufactured, for example, as follows: an azetidinone of the formula

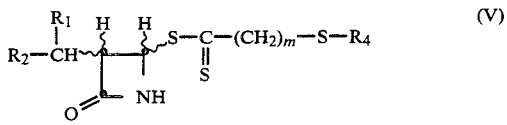

is treated with a compound of the formula $R_3'$—COOH or, especially, with a reactive derivative thereof, such as an acid halide, for example the acid chloride, at a temperature of from 20° to 80° C., preferably at from 40° to 60° C., in an inert solvent, such as one of those mentioned for the reaction of compounds of the formula III to form compounds of the formula I. When using an acid halide the operation is preferably carried out in the presence of an acid-binding agent, such as a tertiary aliphatic amine, for example triethylamine, an aromatic amine, for example pyridine, or especially an alkali metal or alkaline earth metal carbonate or bicarbonate, for example potassium carbonate or calcium carbonate.

In a preferred embodiment of the process, the starting material of the formula III is manufactured as indicated and, without being isolated from the reaction mixture, is reacted with the organic compound of trivalent phosphorus, the end products of the formula I being formed.

(c) Introduction of the heterocyclylthio radical

In a starting material of the formula (IV) the radical Q which can be replaced by nucleophilic reaction preferably represents an esterified hydroxy group, especially a hydroxy group esterified by an optionally oxo-substituted lower alkanecarboxylic acid, for example acetoacetic, formic or acetic acid, by lower alkanesulphonic acid or optionally substituted benzenesulphonic acid, for example methane-, benzene-, 4-bromobenzene- or 4-toluene-sulphonic acid, or by hydrohalic acid, for example hydrochloric, hydrobromic or hydriodic acid. Such radicals Q are, especially, acetoxy, formyloxy, methanesulphonyloxy, p-toluenesulphonyloxy or bromine.

The reaction with a mercaptan of the formula $R_4$—SH can be carried out under neutral conditions in the presence of water and an optionally water-miscible organic solvent. As the water-miscible organic solvent there may be used, for example, lower alkanols, for example methanol or ethanol, lower alkanones, for example acetone, lower alkanecarboxylic acid amides, for example dimethylformamide, or lower alkanecarboxylic acid nitriles, for example acetonitrile. In addition, for example in order to increase the yields, there may be added to the reaction mixture suitable salts, such as alkali metal salts, for example sodium and, especially, potassium salts, of inorganic acids, such as hydrohalic acid, for example hydrochloric acid and, especially, hydriodic acid, as well as thiocyanic acid, or of organic acids, such as lower alkanecarboxylic acids, for example acetic acid, especially potassium iodide and potassium thiocyanate. Salts of suitable anion exchangers with acids, for example acetic acid, for example liquid ion exchangers in salt form, for example Amberlite LA-1 (liquid secondary amines having a molecular weight of from 351 to 393; oil-soluble and water-insoluble; molar equivalents/g=2.5 to 2.7, for example in acetate form) can also be used for this purpose. It is, however, also possible for the reaction to be carried out under weakly basic conditions. The basic conditions can be produced, for example, by the addition of an inorganic base, such as an alkali metal or alkaline earth metal hydroxide, carbonate or bicarbonate, for example sodium, potassium or calcium hydroxide, carbonate or bicarbonate. The reaction is carried out at room temperature, or, depending on the reactivity, while cooling or gently heating, for example at a temperature of from −20° to 80° C.

It is preferable to use those starting materials of the formulae II, III and IV which result in the compounds of the formula I mentioned as being especially preferred at the beginning, especially compounds of the formulae II and III that have a 3S,4R-configuration, or of the formula IV that have a 5R,6S-configuration.

In a resulting compound of the formula I in which one or more functional groups are protected, these groups, for example protected amino, carboxy, hydroxy and/or sulpho groups, may be freed, optionally in stages or simultaneously, in a manner known per se by means of solvolysis, especially hydrolysis, alcoholysis or acidolysis, or by means of reduction, especially hydrogenolysis or chemical reduction.

In a compound of the formula I obtainable according to the invention having a protected amino group, this group may be converted into the free amino group in a manner known per se, for example, according to the nature of the protecting group, preferably by means of solvolysis or reduction. For example, 2-halo-lower alkoxycarbonylamino (optionally after converting a 2-bromo-lower alkoxycarbonylamino group into a 2-iodo-lower alkoxycarbonylamino group), aroylmethoxycarbonylamino or 4-nitrobenzyloxycarbonylamino can be cleaved by treatment with a suitable chemical reducing agent, such as zinc in the presence of a suitable carboxylic acid, such as aqueous acetic acid, or by catalysis with hydrogen in the presence of a palladium catalyst. Aroylmethoxycarbonylamino may be cleaved also by treatment with a nucleophilic, preferably salt-forming reagent, such as sodium thiophenolate, and 4-nitrobenzyloxycarbonylamino may be cleaved also by treatment with an alkali metal dithionite, for example sodium dithionite. Optionally substituted benzyloxycarbonylamino may be cleaved, for example, by means of hydrogenolysis, that is to say by treatment with hydrogen in the presence of a suitable hydrogenation catalyst, such as a palladium catalyst, and allyloxycarbonylamino by reaction with a palladium compound, for example tetrakis(triphenylphosphine)palladium, in the presence of triphenylphosphine and treatment with a carboxylic acid, for example 2-ethylhexanoic acid, or with a salt thereof. An amino group protected by an organic silyl or stannyl group can be freed, for example, by means of hydrolysis or alcoholysis, and an amino group protected by 2-halo-lower alkanoyl, for example 2-chloroacetyl, can be freed by treatment with thiourea in the presence of a base or with a thiolate salt, such as an alkali metal thiolate, of thiourea and subsequent solvolysis, such as alcoholysis or hydrolysis, of the resulting condensation product. An amino group protected by 2-substituted silylethoxycarbonyl can be converted into the free amino group by treatment with a salt of hydrofluoric acid that yields fluoride anions, such as an alkali metal fluoride, for example sodium fluoride, in the presence of a macrocyclic polyether ("Crown ether") or with a fluoride of an organic quaternary base, such as tetra-lower alkylammonium fluoride, for example tetraethylammonium fluoride. An amino group protected in the form of an azido or nitro group is converted into free amino, for example by reduction, for example by catalytic hydrogenation with hydrogen in the presence of a hydrogenation catalyst, such as platinum oxide, palladium or Raney nickel, or by treatment with zinc in the presence of an acid, such as acetic acid. An amino group protected in the form of a phthalimido group can be converted into the free amino group by reaction with hydrazine. Furthermore, an arylthioamino group can be converted into amino by treatment with a nucleophilic reagent, such as sulphurous acid.

In a compound of the formula I obtainable according to the process in which $R_3$ represents a protected carboxy group and/or in which the radical $R_4$ contains protected carboxy as substituent, the carboxy group can be freed in a manner known per se. Thus, tert.-lower alkoxycarbonyl, or lower alkoxycarbonyl substituted in the 2-position by a trisubstituted silyl group or in the 1-position by lower alkoxy, or optionally substituted diphenylmethoxycarbonyl can be converted into free carboxy, for example, by treatment with a carboxylic acid, such as formic acid or trifluoroacetic acid, optionally with the addition of a nucleophilic compound, such as phenol or anisole. Optionally substituted benzyloxycarbonyl can be cleaved, for example, by means of hydrogenolysis, that is to say by treatment with hydrogen in the presence of a metallic hydrogenation catalyst, such as a palladium catalyst. Furthermore, suitably substituted benzyloxycarbonyl, such as 4-nitrobenzyloxycarbonyl, can also be converted into free carboxy by means of chemical reduction, for example by treatment with an alkali metal dithionite, for example sodium dithionite, or with a reducing metal, for example tin, or a reducing metal salt, such as a chromium(II) salt, for example chromium(II) chloride, customarily in the presence of a hydrogen-yielding agent that together with the metal is capable of producing nascent hydrogen, such as a suitable carboxylic acid, for example a lower alkanecarboxylic acid optionally substituted, for example, by hydroxy, for example acetic acid, formic acid or glycolic acid, or an alcohol or thiol, it being preferable to add water. The removal of an allyl protecting group can be effected, for example, by reaction with a palladium compound, for example tetrakis(triphenylphosphine)palladium, in the presence of triphenylphosphine and with the addition of a carboxylic acid, for example 2-ethylhexanoic acid, or a salt thereof. By treatment with a reducing metal or metal salt, as described above, it is also possible to convert 2-halo-lower alkoxycarbonyl (optionally after converting a 2-bromo-lower alkoxycarbonyl group into a corresponding 2-iodo-lower alkoxycarbonyl group), or aroylmethoxycarbonyl into free carboxy, it being possible to cleave aroylmethoxycarbonyl likewise by treatment with a nucleophilic, preferably salt-forming reagent, such as sodium thiophenolate or sodium iodide. Substituted 2-silylethoxycarbonyl can be converted into free carboxy also by treatment with a salt of hydrofluoric acid that yields the fluoride anion, such as an alkali metal fluoride, for example sodium fluoride, in the presence of a macrocyclic polyether ("Crown ether") or with a fluoride of an organic quaternary base, such as tetra-lower alkylammonium fluoride, for example tetrabutylammonium fluoride. Carboxy esterified by an organic silyl or stannyl group, such as tri-lower alkylsilyl or tri-lower alkylstannyl, can be freed in customary manner by solvolysis, for example by treatment with water or an alcohol. A lower alkoxycarbonyl group substituted in the 2-position by lower alkylsulphonyl or cyano can be converted into free carboxy, for example, by treatment with a basic agent, such as an alkali metal or alkaline earth metal hydroxide or carbonate, for example sodium or potassium hydroxide or sodium or potassium carbonate.

In compounds of the formula I obtainable according to the process in which $R_2$ represents a protected hydroxy group and/or in which the radical $R_4$ contains protected hydroxy as substituent, the protected hydroxy group can be converted into the free hydroxy group in a manner known per se. For example, a hydroxy group protected by a suitable acyl group or by an organic silyl or stannyl group can be freed in the same manner as a correspondingly protected amino group: for example a tri-lower alkylsilyl group may be removed with tetrabutylammonium fluoride and acetic acid. (Under these conditions, carboxy groups protected by trisubstituted silylethoxy are not cleaved). A 2-halo-lower alkyl group and an optionally substituted benzyl group are removed by reduction.

A protected, especially esterified, sulpho group is freed in analogous manner to a protected carboxy group.

On the other hand, also compounds of the formula I in which $R_3$ represents carboxy can be converted into compounds of the formula I in which $R_3$ represents a protected carboxy group, especially an esterified carboxy group. Thus, the free carboxy group can be esterified, for example, by treatment with a suitable diazo compound, such as a diazo-lower alkane, for example diazomethane, or a phenyldiazo-lower alkane, for example diphenyldiazomethane, if necessary in the presence of a Lewis acid, such as, for example, boron trifluoride, or by reaction with an alcohol suitable for esterification in the presence of an esterifying agent, such as a carbodiimide, for example dicyclohexyl carbodiimide, and carbonyldiimidazole. Esters can also be manufactured by reaction of a salt of the acid, which salt is optionally produced in situ, with a reactive ester of an alcohol and a strong inorganic acid, such as sulphuric acid, or a strong organic sulphonic acid, such as 4-toluenesulphonic acid. Furthermore, acid halides, such as chlorides, (manufactured, for example, by treatment with oxalyl chloride), activated esters (formed, for example, with N-hydroxynitrogen compounds, such as N-hydroxysuccinimide), or mixed anhydrides (obtained, for example, with haloformic acid lower alkyl esters, such as chloroformic acid ethyl ester or chloroformic acid isobutyl ester, or with haloacetic acid halides, such as trichloroacetyl chloride) can be converted into an esterified carboxy group by reaction with alcohols, optionally in the presence of a base, such as pyridine.

In a compound of the formula I having an esterified carboxy group, this group can be converted into a different esterified carboxy group, for example 2-chloroethoxycarbonyl or 2-bromoethoxycarbonyl may be converted by treatment with an iodine salt, for example sodium iodide, into 2-iodoethoxycarbonyl. Furthermore, in compounds of the formula I that contain a carboxy group protected in esterified form, the carboxy-protecting group can be removed as described above, and a resulting compound of the formula I having a free carboxy group or a salt thereof can be converted by reaction with the reactive ester of a corresponding alcohol into a compound of the formula I in which $R_3$ represents an esterified carboxy group that can be cleaved under physiological conditions.

In compounds of the formula I, in addition, a radical $R_4$ can be converted into a different radical $R_4$.

Thus, for example, in compounds of the formula I in which the heterocyclyl radical $R_4$ is substituted by a carboxy group, this carboxy group can be converted according to processes known per se into a functionally modified carboxy group, such as into an esterified carboxy group or into optionally substituted carbamoyl. For example, by reaction of a compound of the formula I in which $R_4$ represents heterocyclyl substituted by carboxy with an alcohol, especially a lower alkanol, there is obtained a compound of the formula I in which $R_4$ represents heterocyclyl substituted by esterified carboxy, especially lower alkoxycarbonyl, it being preferable to carry out the operation in the presence of a suitable condensation agent, for example a carbodiimide, or to remove the water formed by azeotropic distillation. On the other hand, carboxy groups in radicals $R_4$ can also be converted into reactive functional derivatives, such as mixed anhydrides, for example acid halides, or activated esters, and these can be converted by reaction with an alcohol, for example lower alkanol, ammonia or a primary or secondary amine, for example a lower alkylamine or di-lower alkylamine, into correspondingly esterified or amidated carboxy groups, it being preferable when using mixed anhydrides to carry out the operation in the presence of an acid-binding agent, such as an aromatic or tertiary amine or an alkali metal or alkaline earth metal carbonate.

If a heteroaryl radical $R_4$ contains a hydroxy group, this group may be etherified in customary manner. The reaction to form the corresponding lower alkylheteroaryl ether is effected, for example, in the presence of bases, such as alkali metal hydroxides or carbonates, for example sodium hydroxide or potassium carbonate, with the aid of di-lower alkyl sulphates or lower alkyl halides, or with diazo-lower alkanes, or, in the presence of a dehydrating agent, for example dicyclohexyl carbodiimide, with the aid of lower alkanols. Furthermore, hydroxy may be converted into esterified hydroxy, for example lower alkanoyloxy, for example by reaction with the reactive derivative of a corresponding lower alkanecarboxylic acid, for example acetic acid, such as an anhydride thereof, for example the symmetric anhydride thereof, or a mixed anhydride with a hydrohalic acid, if necessary in the presence of a basic condensation agent, such as an alkali metal hydroxide or carbonate, or a nitrogen base, for example pyridine. The conversion of lower alkanoyloxy into hydroxy is effected, for example, by alcoholysis or, preferably, hydrolysis, for example by base-catalysed hydrolysis, for example in the presence of sodium hydroxide.

In compounds of the formula I in which $R_4$ represents heterocyclyl substituted by amino, the amino group may be converted into a substituted amino group, such as a lower alkylamino, di-lower alkylamino, lower alkyleneamino or lower alkanoylamino group. The conversion into a lower alkylamino or di-lower alkylamino group is effected, for example, by reaction with a reactive esterified lower alkanol, for example with a lower alkyl halide or sulphonate, in the presence of a basic condensation agent, such as a hydroxide or carbonate of an alkali or alkaline earth metal, or a heteroaromatic nitrogen base, for example pyridine. In analogous manner, amino can be converted by treatment with a lower alkylene dihalide or disulphonate into lower alkyleneamino, and by treatment with the reactive functional derivative of a lower alkanecarboxylic acid, for example the corresponding carboxylic acid halide, into lower alkanoylamino.

Salts of compounds of the formula I having salt-forming groups may be manufactured in a manner known per se. Thus, salts of compounds of the formula I having a free carboxy group can be formed, for example, by treatment with metal compounds, such as alkali metal salts of suitable organic carboxylic acids, for example the sodium salt of α-ethylcaproic acid, or with inorganic alkali or alkaline earth metal salts, for example sodium bicarbonate, or with ammonia or with a suitable organic amine, it being preferable to use stoichiometric amounts or only a small excess of the salt-forming agent. Acid addition salts of compounds of the formula I are obtained in customary manner, for example by treatment with a suitable acid or a suitable anion exchange reagent. Internal salts of compounds of the formula I can be formed, for example, by neutralising salts, such as acid addition salts, to the isoelectric point, for example with weak bases, or by treatment with ion exchangers.

Salts can be converted into the free compounds in customary manner; metal and ammonium salts, for example by treatment with suitable acids, and acid addition salts, for example by treatment with a suitable basic agent.

Resulting mixtures of isomers can be separated into the individual isomers according to methods known per se: mixtures of diastereoisomeric isomers, for example by fractional crystallisation, adsorption chromatography (column or thin-layer chromatography) or other suitable separating processes.

The cleaving of resulting racemates into their optical antipodes can be effected in various ways.

One of these ways comprises allowing a racemate to react with an optically active auxiliary, separating the resulting mixture of two diastereoisomeric compounds with the aid of suitable physico-chemical methods and then cleaving the individual diastereoisomeric compounds into the optically active compounds.

Racemates that are especially suitable for separation into the antipodes are those which contain an acidic group, such as, for example, racemates of compounds of the formula I in which $R_3$ represents carboxy. These acidic racemates can be reacted with optically active bases, for example esters of optically active amino acids, or (−)-brucine, (+)-quinidine, (−)-quinine, (+)-cinchonine, (+)-dehydroabietylamine, (+)- and (−)-ephedrin, (+)- and (−)-1-phenylethylamine or their N- mono- or N,N-di-alkylated derivatives, to form mixtures consisting of two diastereoisomeric salts.

In racemates that contain carboxy groups, this carboxy group can also be esterified already or can become esterified by an optically active alcohol, such as (−)-menthol, (+)-borneol, (+)- or (−)-2-octanol, whereupon, when isolation of the desired diastereoisomer is complete, the carboxy group is freed.

For separation of the racemates, the hydroxy group can also be esterified by optically active acids or reactive functional derivatives thereof, diastereoisomeric esters being formed. Such acids are, for example, (−)-abietic acid, D(+)- and L(−)-malic acid, N-acylated optically active amino acid, (+)- and (−)-camphanic acid, (+)- and (−)-ketopinic acid, L(+)-ascorbic acid, (+)-camphoric acid, (+)-camphor-10-sulphonic acid($\beta$), (+)- or (−)-$\alpha$-bromocamphor-$\pi$-sulphonic acid, D(−)-quinic acid, D(−)-isoascorbic acid, D(−)- and L(+)-mandelic acid, (+)-1-menthoxyacetic acid, D(−)- and L(+)-tartaric acid and the di-O-benzoyl and di-O-p-toluyl derivatives thereof.

By reaction with optically active isocyanates, such as with (+)- or (−)-1-phenylethyl isocyanate, it is possible to convert compounds of the formula I in which $R_3$ represents protected carboxy and $R_2$ represents hydroxy into a mixture of diastereoisomeric urethanes.

Basic racemates, for example compounds of the formula I in which the radical $R_4$ is substituted by amino, can form diastereoisomeric salts with the mentioned optically active acids.

The cleaving of the separated diastereoisomers into the optically active compounds of the formula I is also effected according to customary methods. The acids or the bases are freed from the salts, for example, by treatment with acids or bases that are stronger than those originally used. The desired optically active compounds are obtained from the esters and urethanes, for example, after alkaline hydrolysis or after reduction with a complex hydride, such as lithium aluminium hydride.

A further method of separating the racemates comprises chromatography on optically active absorption layers, for example on cane sugar.

According to a third method, the racemates can be dissolved in optically active solvents and the more sparingly soluble optical antipode crystallised out.

A fourth method utilises the different reactivities of the optical antipodes with respect to biological material, such as micro-organisms or isolated enzymes.

According to a fifth method, the racemates are dissolved and one of the optical antipodes is crystallised out by inoculation with a small quantity of an optically active product obtained according to one of the above methods.

The separation of diastereoisomers into the individual racemates and of the racemates into the optical antipodes can be carried out at any stage of the process, that is to say, for example, even at the stage of the starting compounds of the formulae II to IV or at any stage of the process for the manufacture of the starting compounds of the formula II or IV that is described hereinafter.

In all subsequent conversions of resulting compounds of the formula I, those reactions are preferred which take place under neutral, alkaline or weakly acidic conditions.

The process also includes those embodiments according to which compounds formed as intermediates are used as starting materials and the remaining process steps are carried out with them, or the process is discontinued at any stage. Furthermore, starting materials can be used in the form of derivatives or can be formed in situ, optionally under the reaction conditions. For example, a starting material of the formula II in which Z represents oxygen can be manufactured in situ from a compound of the formula II in which Z represents an optionally substituted methylidene group, as described hereinafter, by ozonisation and subsequent reduction of the ozonide formed, analogously to the process (Stage 3.3) described hereinafter, whereafter the cyclisation to form the compound of the formula I is effected in the reaction solution.

The starting compounds of the formulae II, IV and V and the precursors can be manufactured as indicated in reaction schemes I, II and III.

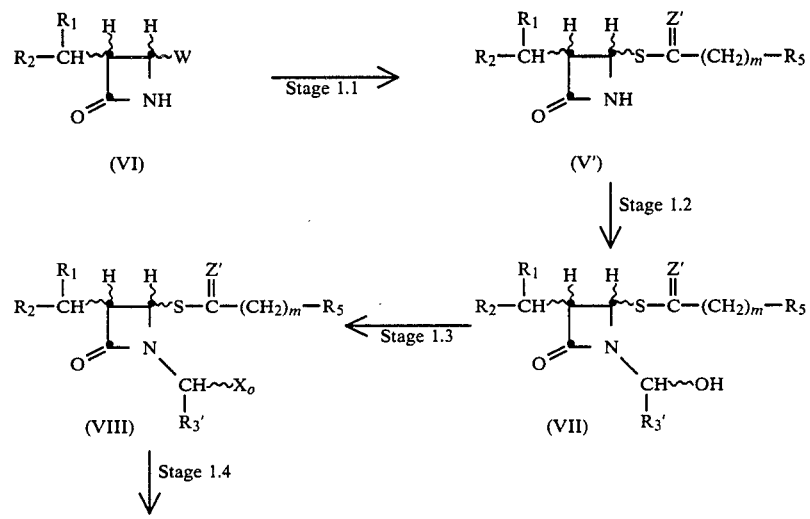

Reaction Scheme I

-continued

Reaction Scheme I

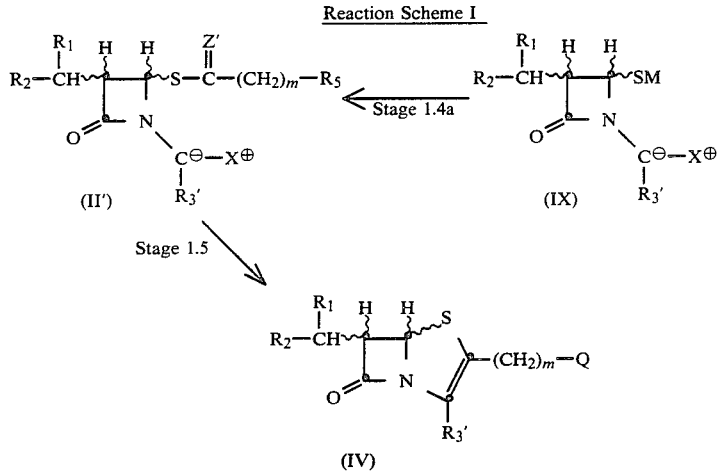

In the compounds of the formulae V', VII, VIII and II', Z' represents oxygen, sulphur or alternatively a methylidene group that is optionally substituted by one or two substituents Y and can be converted by oxidation into an oxo group Z. A substituent Y of this methylidene group is an organic radical, for example optionally substituted lower alkyl, for example methyl or ethyl, cycloalkyl, for example cyclopentyl or cyclohexyl, phenyl or phenyl-lower alkyl, for example benzyl, or, especially, an esterified carboxy group, including a carboxy group esterified by an optically active alcohol, such as l-menthol, for example one of the optionally substituted lower alkoxycarbonyl or arylmethoxycarbonyl radicals mentioned under $R_3$ or alternatively l-menthyloxycarbonyl. The methylidene group Z' preferably carries one of the mentioned substituents. Special mention should be made of the methoxycarbonylmethylidene, ethoxycarbonylmethylidene and the l-menthyloxycarbonylmethylidene group Z'. The latter can be used for the manufacture of optically active compounds of the formulae V', VII, VIII and II'.

In the compounds of the formulae V', VII, VIII and II', $R_5$ represents either the radical —$SR_4$ or a reactive esterified hydroxy group Q.

In the compounds of the formulae V' to IX and II', the radical $R_2$ is preferably one of the mentioned protected hydroxy groups, for example optionally substituted 1-phenyl-lower alkoxy, optionally substituted phenyl-lower alkoxycarbonyloxy, or trisubstituted silyloxy.

Stage 1.1

A thioazetidinone of the formula V' is obtained by treating a 4-W-azetidinone of the formula VI in which W represents a nucleofugal leaving group with a mercapto compound of the formula

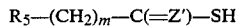

or with a salt, for example an alkali metal salt, such as a sodium or potassium salt, thereof, and, if desired, in a resulting compound of the formula V', in which $R_2$ represents hydroxy, converting hydroxy into protected hydroxy.

The nucleofugal leaving group W in a starting material of the formula VI is a radical that can be replaced by the nucleophilic radical

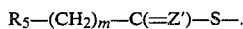

Such groups W are, for example, acyloxy radicals, sulphonyl radicals $R_o$—$SO_2$— in which $R_o$ is an organic radical, or azido or halogen. In an acyloxy radical W, acyl is, for example, the radical of an organic carboxylic acid, including an optically active carboxylic acid, and represents, for example, lower alkanoyl, for example acetyl or propionyl, optionally substituted benzoyl, for example benzoyl or 2,4-dinitrobenzoyl, phenyl-lower alkanoyl, for example phenylacetyl, or the acyl radical of one of the above-mentioned optically active acids. In a sulphonyl radical $R_o$—$SO_2$—, $R_o$ is, for example, lower alkyl optionally substituted by hydroxy, such as methyl, ethyl or 2-hydroxyethyl, and also correspondingly substituted optically active lower alkyl, for example (2R)- or (2S)-1-hydroxyprop-2-yl, methyl substituted by an optically active radical, such as camphoryl, or benzyl, or optionally substituted phenyl, such as phenyl, 4-bromophenyl or 4-methylphenyl. A halogen radical W is, for example, bromine, iodine or, especially, chlorine. W is preferably methyl- or 2-hydroxyethyl-sulphonyl, acetoxy or chlorine.

The nucleophilic substitution can be carried out under neutral or weakly basic conditions in the presence of water and, optionally, a water-miscible organic solvent. The basic conditions can be produced, for example, by the addition of an inorganic base, such as an alkali metal or alkaline earth metal hydroxide, carbonate or bicarbonate, for example sodium, potassium or calcium hydroxide, carbonate or bicarbonate. As organic solvents there may be used, for example, water-miscible alcohols, for example lower alkanols, such as methanol or ethanol, ketones, for example lower alkanones, such as acetone, amides, for example lower alkanecarboxylic acid amides, such as dimethylformamide, acetonitrile and the like. The reaction is customarily carried out at room temperature but may also be carried out at elevated or reduced temperature. The reaction can be accelerated by the addition of a salt of hydriodic acid or of thiocyanic acid, for example an alkali metal salt, such as a sodium salt.

It is possible to use in the reaction optically inactive cis- or trans-compounds of the formula VI and mixtures thereof, or corresponding optically active compounds. The group being introduced, $R_5$—$(CH_2)_m$—C(=Z')—S—, is directed by the group $(R_1,R_2)CH$— preferentially into the trans-position, irrespective of whether W is in the cis- or trans-position to the group $(R_1,R_2)CH$—. Although predominantly the trans-isomers are formed, it is occasionally possible also to isolate the cis-isomers. The separation of the cis- and trans-isomers is effected as described above, according to conventional methods, especially by chromatography and/or by crystallisation.

The subsequent ozonisation of a methylidene group Z' can be effected as described hereinafter. A resulting racemate of the formula V' can be separated into the optically active compounds.

An azetidinone of the formula VI in which $R_2$ and W each represents acetoxy and $R_1$ represents hydrogen is described in German Offenlegungsschrift No. 29 50 898.

Other azetidinones of the formula VI can be manufactured according to methods known per se, for example by reacting a vinyl ester of the formula $(R_1,R_2)CH$—CH=CH—W with chlorosulphonyl isocyanate and reacting the resulting cyclo adduct with a reducing agent, for example sodium sulphite. In this synthesis, mixtures of cis- and trans-isomers are customarily obtained which, if desired, can be separated into the pure cis- or trans-isomers, for example by chromatography and/or crystallisation or distillation. The pure cis- and trans-isomers are present in the form of racemates and can be separated into their optical antipodes, for example if acyl in an acyloxy radical W in compounds of the formula VI originates from an optically active acid. The compounds of the formula VI, especially their optically active forms, can also be manufactured according to the processes given below in reaction schemes II and III.

Stage 1.2

An α-hydroxycarboxylic acid compound of the formula VII is obtained by reacting a compound of the formula V' with a glyoxylic acid compound of the formula OHC—$R_3'$ or with a suitable derivative thereof, such as a hydrate, hemihydrate or semiacetal, for example a semiacetal with a lower alkanol, for example methanol or ethanol, and, if desired, in a resulting compound of the formula VII in which $R_2$ represents hydroxy, converting hydroxy into protected hydroxy.

The compound of the formula VII is customarily obtained in the form of a mixture of the two isomers (with respect to the $>CH{\sim}OH$ grouping). It is also possible, however, to isolate the pure isomers thereof.

The addition of the glyoxylic acid ester compound to the nitrogen atom of the lactam ring is effected at room temperature or, if necessary, while heating, for example up to approximately 100° C., and in the absence of a true condensation agent and/or without formation of a salt. When using the hydrate of the glyoxylic acid compound, water is formed which, if necessary, is removed by distillation, for example azeotropically, or by using a suitable dehydrating agent, such as a molecular sieve. It is preferable to carry out the operation in the presence of a suitable solvent, such as, for example, dioxan, toluene or dimethylformamide, or a solvent mixture, if desired or necessary in the atmosphere of an inert gas, such as nitrogen.

It is possible to use in the reaction pure optically inactive cis- or trans-compounds of the formula V' and mixtures thereof, or corresponding optically active compounds. A resulting racemate of the formula VII can be separated into the optically active compounds.

Stage 1.3

Compounds of the formula VIII in which $X_o$ represents a reactive esterified hydroxy group, especially halogen or organic sulphonyloxy, are manufactured by, in a compound of the formula VII, converting the secondary hydroxy group into a reactive esterified hydroxy group, especially into halogen, for example chlorine or bromine, or into an organic sulphonyloxy group, such as lower alkanesulphonyloxy, for example methanesulphonyloxy, or arenesulphonyloxy, for example benzene- or 4-methylbenzene-sulphonyloxy.

In the starting compounds of the formula VII, $R_2$ preferably represents a protected hydroxy group.

The compounds of the formula VIII can be obtained in the form of mixtures of the isomers (with respect to the $>CH{\sim}X_o$ grouping) or in the form of pure isomers.

The above reaction is carried out by treatment with a suitable esterifying agent, for example with a thionyl halide, for example the chloride, a phosphorus oxyhalide, especially the oxychloride, a halophosphonium halide, such as triphenyl phosphono-dibromide or -diiodide, or a suitable organic sulphonic acid halide, such as the chloride, preferably in the presence of a basic agent, especially an organic basic agent, such as an aliphatic tertiary amine, for example triethylamine, diisopropylethylamine or "polystyrene Hünig base" or a heterocyclic base of the pyridine type, for example pyridine or collidine. The operation is preferably carried out in the presence of a suitable solvent, for example dioxan or tetrahydrofuran, or a solvent mixture, if necessary while cooling and/or in the atmosphere of an inert gas, such as nitrogen.

In a compound of the formula VIII obtainable in this manner, a reactive esterified hydroxy group $X_o$ can be converted into a different reactive esterified hydroxy group in a manner known per se. Thus, for example, a chlorine atom can be replaced by a bromine or iodine atom by treatment of the corresponding chlorine compound with a suitable bromide or iodide salt, such as lithium bromide or iodide, preferably in the presence of a suitable solvent, such as ether.

It is possible to use in the reaction pure optically inactive cis- or trans-compounds of the formula VII and mixtures thereof, or corresponding optically active compounds. A resulting racemate of the formula VIII can be separated into the optically active compounds.

Stage 1.4

The starting material of the formula II' is obtained by treating a compound of the formula VIII in which $X_o$ represents a reactive esterified hydroxy group with a suitable phosphine compound, such as a tri-lower alkylphosphine, for example tri-n-butylphosphine, or a triarylphosphine, for example triphenylphosphine, or with a suitable phosphite compound, such as a tri-lower alkyl phosphite, for example triethyl phosphite, or an alkali metal di-lower alkyl phosphite, for example diethyl phosphite, it being possible, depending upon the reagent chosen, to obtain a compound of the formula II (or II') or IIa.

The above reaction is preferably carried out in the presence of a suitable inert solvent, such as a hydrocarbon, for example hexane, cyclohexane, benzene, toluene or xylene, or an ether, for example dioxan, tetrahydrofuran or diethylene glycol dimethyl ether, or a solvent mixture. Depending upon reactivity, the operation is carried out while cooling or at elevated temperature, approximately between −10° and +100° C., preferably at approximately 20° to 80° C., and/or in the atmosphere of an inert gas, such as nitrogen. In order to prevent oxidative processes taking place catalytic amounts of an antioxidant, for example hydroquinone, can be added.

When using a phosphine compound, the operation is customarily carried out in the presence of a basic agent, such as an organic base, for example an amine, such as triethylamine, diisopropylethylamine or "polystyrene Hünig base", and there is thus obtained directly the ylide starting material of the formula II (or II') which is formed from the corresponding phosphonium salt.

It is possible to use in the reaction pure, optically inactive cis- or trans-compounds of the formula VIII and mixtures thereof, or corresponding optically active compounds. A resulting racemate of the formula II' can be separated into the optically active compounds.

Stage 1.4a

A starting compound of the formula II' in which Z' represents oxo can furthermore be obtained by treating a mercaptide of the formula IX, in which M represents a metal cation, with an acylating agent that introduces the radical $R_5—(CH_2)_m—C(=O)—$.

In the starting material of the formula IX, the metal cation M is, for example, a cation of the formula $M^+$ or $M^{2+}/2$, in which $M^+$ represents especially a silver cation and $M^{2+}$ represents especially the divalent cation of a suitable transition metal, for example copper, lead or mercury.

An acylating agent that introduces the radical $R_5—(CH_2)_m—C(=O)—$ is, for example, the acid $R_5—(CH_2)_m—COOH$ or a reactive functional derivative thereof, such as an acid halide, for example chloride or bromide, or an azide or anhydride thereof.

The acylation is carried out, if the free acid of the formula $R_5—(CH_2)_m—COOH$ is used, for example in the presence of a suitable water-removing agent, such as a carbodiimide, for example N,N'-dicyclohexyl carbodiimide, or, if an acid derivative is used, in the presence of a suitable acid-binding agent, such as a tertiary aliphatic or aromatic base, for example triethylamine, pyridine or quinoline, in an inert solvent, such as a chlorinated hydrocarbon, for example methylene chloride, or an ether, for example diethyl ether or dioxan, at room temperature or while heating or cooling, for example in a temperature range of from approximately −50° to approximately +60° C., especially at from approximately −30° to approximately +20° C.

The starting compounds of the formula IX can be manufactured, for example, by converting an azetidinone of the formula

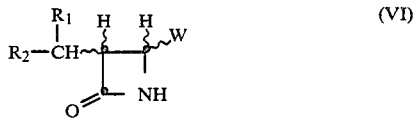

(VI)

by reaction with an alkali metal salt, for example the sodium salt, of a thio-lower alkanecarboxylic acid, for example thioacetic acid, or of a triphenylmethylmercaptan, into a compound of the formula

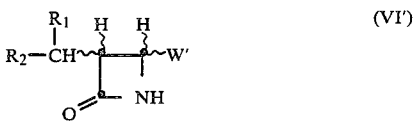

(VI')

in which W' represents triphenylmethylthio or lower alkanoylthio, for example acetylthio, converting this, analogously to the process described in reaction stages 1.2, 1.3 and 1.4, into a compound of the formula

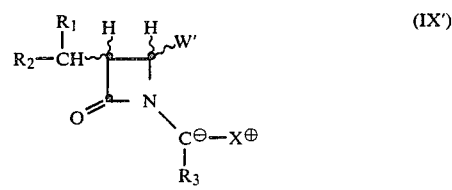

(IX')

and reacting this, in the presence of a base, for example pyridine or tri-n-butylamine, in a suitable solvent, for example diethyl ether or methanol, with a salt of the formula MA, in which M has the meaning given above but represents especially a silver cation, and A represents a customary anion that favours the solubility of the salt MA in the chosen solvent, for example the nitrate, acetate or fluoride anion.

Compounds of the formula (II') in which $R_5$ represents a reactive esterified hydroxy group can be converted by reaction with a mercaptan of the formula $R_4—SH$ into compounds of the formula (II') in which $R_5$ represents the radical $—SR_4$, for example the reaction conditions given above in process (c) being used.

The ylides of the formula II' in which Z' represents oxygen or sulphur can be used directly in the cyclisation reaction for the manufacture of the end products of the formula I. It is also possible, however, in compounds of the formula II' in which $R_2$ represents a protected hydroxy group, for example a protected hydroxy group that can readily be cleaved by hydrolysis, such as trisubstituted silyloxy, first to remove the hydroxy-protecting group and then to use the resulting compound of the formula II' in which $R_2$ represents hydroxy in the cyclisation reaction.

In the compounds of the formulae II', V', VII and VIII, an optionally substituted methylidene group Z' can be converted into the oxo group Z by ozonisation and subsequent reduction of the ozonide formed, according to the process described hereinafter in stage 3.3.

Stage 1.5

The starting compound of the formula (IV) is obtained by the cyclisation of an ylide of the formula (II') in which Z' represents oxygen or sulphur and $R_5$ represents a reactive esterified hydroxy groups Q.

The cyclisation can be carried out, for example, in the same manner as is described for the manufacture of compounds of the formula (I) from the ylides of the formula (II) (process a).

Starting compounds of the formula VI in which W represents a sulphonyl radical $HO—A—SO_2—$ can also be manufactured according to the following reaction scheme II.

Reaction Scheme II

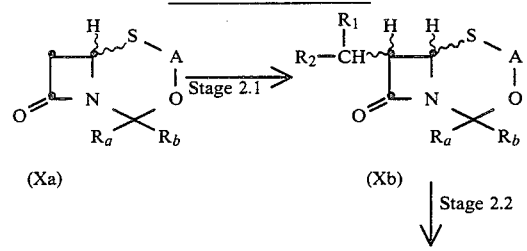

(Xa)     (Xb)

Stage 2.2

-continued
Reaction Scheme II

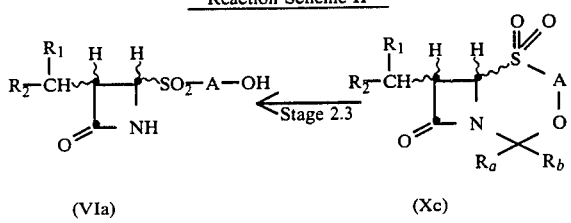

(VIa) (Xc)

In the compounds of the formulae (Xa) to (Xc) and (VIa), A represents a lower alkylene radical having 2 or 3 carbon atoms between the two hetero atoms and represents especially ethylene or 1,2-propylene, but may also represent 1,3-propylene, 1,2-, 2,3- or 1,3-butylene.

In the compounds of the formulae (Xa) to (Xc), each of the radicals $R_a$ and $R_b$ represents hydrogen or an organic radical bonded via a carbon atom to the ring carbon atom, it being possible for the two radicals $R_a$ and $R_b$ to be linked to one another, and represents especially hydrogen, lower alkyl, for example methyl, ethyl, n-propyl, or isopropyl, optionally substituted phenyl, or phenyl-lower alkyl, for example benzyl, or, if taken together, represent lower alkylene preferably having from 4 to 6 carbon atoms, for example 1,4-butylene or 1,5-pentylene.

In the compounds of the formulae (Xb), (Xc) and (VIa), the radical $R_2$ represents hydroxy or, preferably, one of the mentioned protected hydroxy groups, for example optionally substituted 1-phenyl-lower alkoxy, optionally substituted phenyl-lower alkoxycarbonyloxy or trisubstituted silyloxy.

Stage 2.1

A compound of the formula (Xb) is obtained by reacting a bicyclic compound of the formula (Xa) with a metallating reagent and an electrophilic agent that introduces the radical $(R_1,R_2)CH—$, then treating the resulting product with a proton source.

Suitable metallating reagents are, for example, substituted and unsubstituted alkali metal amides, alkali metal hydrides or alkali metal-lower alkyl compounds in which the alkali metal is, for example, sodium or, especially, lithium, for example sodium or lithium amide, lithium bis-trimethylsilylamide, sodium hydride, lithium hydride and, preferably, lithium diisopropylamide and butyllithium.

Electrophilic agents that introduce the radical $(R_1,R_2)CH—$ are, for example, compounds of the formula $R_1—CH=O$ or functional derivatives thereof of the formula $(R_1,R_2)CH—X$ in which X represents a nucleofugal leaving group, especially halogen, for example chlorine, bromine or iodine, or sulphonyloxy, for example methanesulphonyloxy or 4-toluenesulphonyloxy. Preferred electrophilic agents that introduce the radical $(R_1,R_2)CH—$ are formaldehyde, and optionally substituted benzyloxymethyl chloride and acetaldehyde.

Solvents suitable for the metallating reaction should not contain active hydrogen and are, for example, hydrocarbons, for example hexane, benzene, toluene or xylene, ethers, for example diethyl ether, tetrahydrofuran or dioxan, or acid amides, for example hexamethylphosphoric acid triamide.

The metallated intermediate need not be isolated but, subsequent to the metallating reaction, can be reacted with an electrophilic agent that introduces the radical $(R_1,R_2)CH—$. The metallating reaction takes place at temperatures of from approximately $-100°$ C. to approximately room temperature, preferably at below $-30°$ C., and preferably in an inert gas atmosphere, such as a nitrogen atmosphere. The further reaction can take place under the same conditions. Formaldehyde is introduced into the reaction mixture preferably in gaseous, monomeric form. Monomeric formaldehyde can be obtained, for example, by thermal depolymerisation of paraformaldehyde or by thermal decomposition of formaldehydecyclohexyl hemiacetal.

It is possible to use for the metallating reaction both the individual antipodes of compounds of the formula (Xa) and their racemic or diastereoisomeric mixtures.

The action of the electrophilic agent that introduces the radical $(R_1,R_2)CH—$ on the substrate generally takes place stereospecifically. If there is used as starting material an azetidinone of the formula (Xa) having the R-configuration at carbon atom 4 of the azetidinone ring, there is produced predominantly a compound of the formula (Xb) having the R-configuration at carbon atom 4 and the S-configuration at carbon atom 3 of the azetidinone ring, that is to say the action of the electrophilic agent takes place predominantly in the trans-position.

After the reaction, the reaction product is treated with a proton source, for example with water, an alcohol, such as methanol or ethanol, an organic or inorganic acid, for example acetic acid, hydrochloric acid, sulphuric acid, or a similar compound that yields protons, again preferably at low temperatures.

In a resulting compound of the formula (Xb) in which $R_2$ represents hydrogen, the hydroxy group can be protected in a manner known per se, for example by etherification or esterification, especially as described above.

The manufacture of optically active and optically inactive starting compounds of the formula (Xa) is described, for example, in European Patent Application No. 23887.

Stage 2.2

A sulphone of the formula (Xc) can be manufactured by treating a thio compound of the formula (Xb) with an oxidising agent and, if desired, converting a compound of the formula (Xc) obtainable according to the process in which $R_2$ represents hydroxy into a compound of the formula (Xc) in which $R_2$ represents a protected hydroxy group.

Suitable oxidising agents are, for example, hydrogen peroxide, organic peracids, especially aliphatic or aromatic percarboxylic acids, for example peracetic acid, perbenzoic acid, chloroperbenzoic acid, for example 3-chloroperbenzoic acid, or monoperphthalic acid, oxidising inorganic acids and salts thereof, for example nitric acid, chromic acid, potassium permanganate, or alkali metal hypochlorites, for example sodium hypochlorite. The conversion may, however, also be effected by anodic oxidation.

The oxidation is preferably carried out in a suitable inert solvent, for example a halogenated hydrocarbon, for example methylene chloride, chloroform or carbon tetrachloride, an alcohol, for example methanol or ethanol, a ketone, for example acetone, an ether, for example diethyl ether, dioxan or tetrahydrofuran, an amide, for example dimethylformamide, a sulphone, for example dimethylsulphone, a liquid organic carboxylic acid, for example acetic acid, or in water or in a mixture of these solvents, especially a water-containing mixture, for example aqueous acetic acid, and at room temperature, or while cooling or gently heating, that is to say at from approximately −20° to approximately +90° C., but preferably at approximately room temperature. The oxidation may also be carried out in steps by first, at low temperature, that is to say at from approximately −20° to approximately 0° C., oxidising to the sulphoxide, which is optionally isolated, and then, in a second step preferably carried out at elevated temperature, for example at room temperature, oxidising the sulphoxide to form the sulphone of the formula (Xc).

For working up, excess oxidising agent which may still be present can be destroyed by reduction, especially by treatment with a reducing agent, such as a thiosulphate, for example sodium thiosulphate.

It is possible to use in the reaction both optically inactive compounds of the formula (Xb) and corresponding optically active compounds, especially those having the 3S,4R-configuration in the azetidinone ring.

Stage 2.3

Compounds of the formula (VIa) can be manufactured by solvolysing a bicyclic amide of the formula (Xc) with a suitable solvolysis reagent and, if desired, in a compound of the formula (VIa) obtainable according to the process, converting a free hydroxy group $R_2$ into a protected hydroxy group $R_2$.

Suitable solvolysis reagents are, for example, organic acids, for example lower alkanecarboxylic acids, such as formic acid or acetic acid, or sulphonic acids, for example 4-toluenesulphonic acid or methanesulphonic acid, mineral acids, for example sulphuric or hydrochloric acid, and also lower alkanols, for example methanol or ethanol, or lower alkanediols, for example ethylene glycol.

The mentioned solvolysis reagents are added undiluted or diluted with water. The solvolysis can also be carried out with pure water. The solvolysis with the acidic reagent is preferably effected in an aqueous solution of this reagent and at temperatures of from approximately −20° to approximately 150° C., preferably at from room temperature to 110° C.

It is possible to use in the reaction both optically inactive compounds of the formula (Xc), for example racemates or diastereoisomeric mixtures, and corresponding optically active compounds, especially those having the 3S,4R-configuration in the azetidinone ring.

Resulting isomeric mixtures of compounds of the formulae (Xb), (Xc) and (VIa), such as racemates or diastereoisomeric mixtures, can be separated into the individual isomers, such as antipodes, in a manner known per se, for example as described above.

Optically active trans-compounds of the formula (VI) that can be used according to the invention can be manufactured also according to the following reaction scheme III:

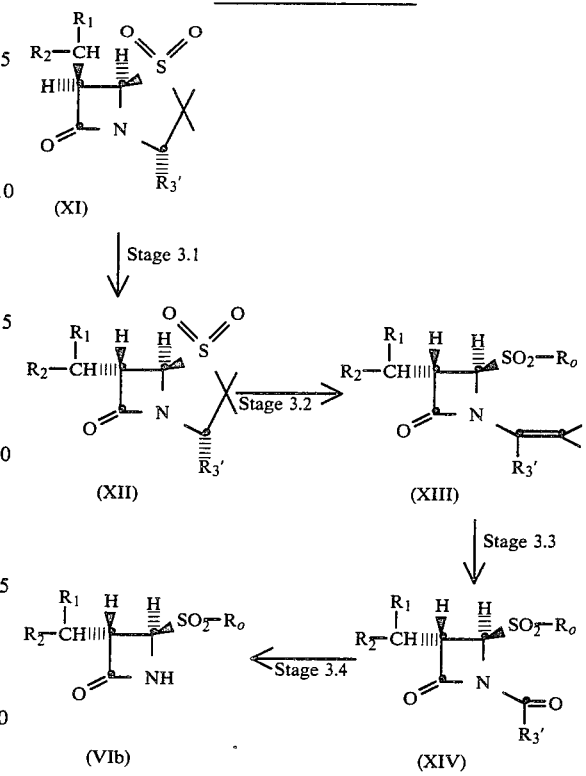

Reaction Scheme III

In the compounds of the formulae (XI) to (XIV) and (VIb), $R_2$ represents hydroxy or, especially, a protected hydroxy group.

Stage 3.1

Compounds of the formula (XII) are known or can be manufactured in a manner known per se. They can also be manufactured according to a novel process by epimerising a compound of the formula (XI) and, if desired, in a compound of the formula (XII) obtainable according to the process, converting a protected hydroxy group $R_2$ into a different protected hydroxy group $R_2$.

The epimerisation is effected, for example, in the presence of a basic agent, such as an amine, for example a tri-lower alkylamine, for example triethylamine or ethyldiisopropylamine, a tertiary amine, for example N,N-dimethylaniline, an aromatic amine, for example pyridine, or a bicyclic amine, for example 1,5-diazabicyclo[5.4.0]undec-5-ene or 1,5-diazabicyclo[4.3.0]non-5-ene, or an alkali metal-lower alkoxide, for example sodium methoxide, sodium ethoxide or potassium tert.-butoxide, in an inert solvent, for example an ether, for example diethyl ether, dimethoxyethane, tetrahydrofuran or dioxan, acetonitrile or dimethylformamide, optionally at slightly elevated or reduced temperature, for example at from 0° to 50° C., but preferably at room temperature.

In the compounds of the formula (XII) obtainable according to the process, a protected hydroxy group $R_2$ can be replaced by a different protected hydroxy group $R_2$, for example a protected hydroxy group that can be cleaved by hydrogenolysis can be replaced by a protected hydroxy group that can be cleaved by solvolysis. Hydroxy-protecting groups are especially the above-mentioned protecting groups that can be removed by hydrogenolysis, for example 1-phenyl-lower alkyl or phenyl-lower alkoxycarbonyl, each substituted as indicated, or protecting groups that can be removed by solvolysis, for example silyl trisubstituted as indicated.

The reaction can be carried out by first removing the hydroxy-protecting group that can be removed by hydrogenolysis and then introducing into the resulting compound of the formula XII in which $R_2$ represents hydroxy, a hydroxy-protecting group that can be removed by solvolysis.

The removal of a protecting group that can be removed by hydrogenolysis is effected, for example, with hydrogen or a hydrogen-donor, for example cyclohexene or cyclohexadiene, in the presence of a hydrogenation catalyst, such as a palladium catalyst, for example palladium-on-carbon, in an inert solvent, such as a halogenated hydrocarbon, for example methylene chloride, a lower alkanol, for example methanol or ethanol, an ether, for example dioxan or tetrahydrofuran, or alternatively in water or in mixtures thereof, at a temperature of from approximately 0° to approximately 80° C., preferably at room temperature. The removal can also be carried out with a reducing metal, such as zinc, or a reducing metal alloy, for example a copper/zinc alloy, in the presence of an agent that yields protons, such as an organic acid, for example acetic acid, or alternatively a lower alkanol, for example ethanol.

The introduction of a hydroxy-protecting group that can be removed by solvolysis is effected, for example, with a compound of the formula $R_2'$—$X_3$ in which $R_2'$ represents the hydroxy-protecting group and $X_3$ represents, for example, a reactive esterified hydroxy group, for example halogen, for example chlorine, bromine or iodine, or sulphonyloxy, such as methanesulphonyloxy, benzenesulphonyloxy or 4-toluenesulphonyloxy.

The reaction is effected in an inert solvent, such as an ether, for example diethyl ether, dioxan or tetrahydrofuran, a hydrocarbon, for example benzene or toluene, a halogenated hydrocarbon, for example methylene chloride, in dimethyl sulphoxide or acetonitrile, in the presence of a basic condensation agent, such as an alkali metal hydroxide or carbonate, for example sodium or potassium hydroxide or sodium or potassium carbonate, an alkali metal amide or hydride, for example sodium amide or sodium hydride, an alkali metal lower alkoxide, for example sodium methoxide or ethoxide or potassium tert.-butoxide, or an amine, for example triethylamine, pyridine or imidazole, at room temperature or at elevated or reduced temperature, for example at from approximately −20° to approximately 80° C., but preferably at room temperature.

Starting compounds of the formula (XI) are known, for example, from German Offenlegungsschrift No. 3 039 504 and from British Patent Application No. 20 61 930.

Stage 3.2

A compound of the formula (XIII) can be manufactured by treating a penam compound of the formula (XII) with a basic agent and with an esterifying agent that introduces the radical $R_o$.

A suitable basic agent is, for example, one of the basic agents mentioned under stage 3.1, especially one of the mentioned bicyclic amines, and also an alkali metal amide or hydride, for example sodium amide or sodium hydride.

A radical $R_o$ is, for example, one of the organic radicals mentioned under stage 1.1, especially optionally substituted lower alkyl, for example methyl, ethyl or 2-hydroxyethyl, or benzyl.

An esterifying agent that introduces the radical $R_o$ is, for example, a compound of the formula $R_o$—$X_4$ in which $X_4$ represents reactive esterified hydroxy, for example halogen, such as chlorine, bromine or iodine, or sulphonyloxy, such as methanesulphonyloxy, benzenesulphonyloxy or 4-toluenesulphonyloxy. For the introduction of a 2-hydroxyethyl radical, ethylene oxide is also suitable.

The reaction is preferably carried out in two steps; in the first step the penam compound of the formula (XII) is treated with at least equimolar amounts of the basic agent and a resulting intermediate of the formula

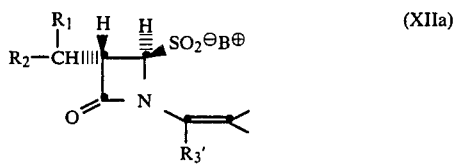

in which B⊕ represents the protonated form (cation) of the basic agent, is reacted with the esterifying agent, preferably without being isolated from the reaction mixture. The reaction is carried out in an inert solvent, for example an ether, for example diethyl ether, dimethoxyethane, tetrahydrofuran or dioxan, in acetonitrile, dimethylformamide or hexamethylphosphoric acid triamide, optionally at slightly elevated or reduced temperature, for example at approximately 0° to 50° C., but preferably at room temperature. In a preferred embodiment of the process, the penam compound of the formula (XII) is manufactured in situ by, as described in stage 3.1, first treating a compound of the formula (XI) with catalytic amounts of the basic agent, for example 1,5-diazabicyclo[5.4.0]undec-5-ene, and then reacting the product with at least equimolar amounts of the same basic agent and the esterifying agent to form the compounds of the formula (XIII).

Stage 3.3

An oxalylazetidinone of the formula (XIV) can be manufactured by ozonising a compound of the formula (XIII) and cleaving the ozonide formed by reduction to form the oxo compound.

The ozonisation is customarily carried out with a mixture of ozone and oxygen in an inert solvent, such as a lower alkanol, for example methanol or ethanol, a lower alkanone, for example acetone, an optionally halogenated hydrocarbon, for example a halo-lower alkane, such as methylene chloride or carbon tetrachloride, or in a solvent mixture, including an aqueous mixture, preferably while cooling, for example at temperatures of from approximately −80° to approximately 0° C.

An ozonide obtained as intermediate is cleaved by reduction, customarily without being isolated, to form a compound of the formula XIV, there being used catalytically activated hydrogen, for example hydrogen in the presence of a heavy metal hydrogenation catalyst, such as a nickel catalyst and also a palladium catalyst, preferably on a suitable carrier, such as calcium carbonate or carbon, or chemical reducing agents, such as reducing heavy metals, including heavy metal alloys or amalgams, for example zinc, in the presence of a hydrogen-donor, such as an acid, for example acetic acid, or an alcohol, for example lower alkanol, reducing inorganic salts, such as alkali metal iodides, for example sodium iodide, or alkali metal bisulphites, for example sodium bisulphite, in the presence of a hydrogen-donor, such as an acid, for example acetic acid, or water, or reducing organic compounds, such as formic acid. As reducing agents there may also be used compounds that can readily be converted into corresponding epoxide compounds or oxides, it being possible for the epoxide formation to be effected as a result of a C—C double bond and the oxide formation in view of the presence of an oxide-forming hetero atom, such as a sulphur, phosphorus or nitrogen atom. Such compounds are, for example, suitably substituted ethene compounds (which are converted into ethylene oxide compounds in the reaction), such as tetracyanoethylene; or, especially, suitable sulphide compounds (which are converted into sulphoxide compounds in the reaction), such as di-lower alkyl sulphides, especially dimethyl sulphide; suitable organic phosphorus compounds, such as a phosphine optionally substituted by phenyl and/or lower alkyl, for example methyl, ethyl, n-propyl or n-butyl (which phosphine is converted into a phosphine oxide in the reaction), such as tri-lower alkylphosphines, for example tri-n-butylphosphine, or triphenylphosphine; and also tri-lower alkyl phosphites (which are converted into phosphoric acid tri-lower alkyl esters in the reaction), customarily in the form of corresponding alcohol adduct compounds, such as trimethyl phosphite, or phosphorous acid triamides, which optionally contain lower alkyl as substituent, such as hexa-lower alkyl phosphorous acid triamides, for example hexamethylphosphorous acid triamide, the latter preferably being in the form of a methanol adduct; and also suitable nitrogen bases (which are converted into the corresponding N-oxides in the reaction), such as heterocyclic nitrogen bases of aromatic character, for example bases of the pyridine type and, especially, pyridine itself. The cleaving of the ozonide, which customarily is not isolated, is normally effected under the same conditions as those used for its manufacture, that is to say, in the presence of a suitable solvent or solvent mixture, and while cooling or heating gently, the operation preferably being carried out at temperatures of from approximately $-10°$ to approximately $+25°$ C., and the reaction customarily being concluded at room temperature.

Stage 3.4

An azetidinone of the formula (VIb) can be manufactured by solvolysing an oxalylazetidinone of the formula (XIV).

The solvolysis can be carried out in the form of hydrolysis, alcoholysis or alternatively in the form of hydrazinolysis. Hydrolysis is carried out with water, optionally in a water-miscible solvent. Alcoholysis is customarily carried out with a lower alkanol, for example methanol or ethanol, preferably in the presence of water and an organic solvent, such as a lower alkanecarboxylic acid lower alkyl ester, for example ethyl acetate, preferably at room temperature, if necessary while cooling or heating, for example at a temperature of from approximately 0° to approximately 80° C. Hydrazinolysis is carried out in conventional manner with a substituted hydrazine, for example with phenyl- or a nitrophenyl-hydrazine, such as 2-nitrophenylhydrazine, 4-nitrophenylhydrazine or 2,4-dinitrophenylhydrazine, which is preferably used in an approximately equimolar amount, in an organic solvent, such as an ether, for example tetrahydrofuran, dioxan, diethyl ether, an aromatic hydrocarbon, such as benzene or toluene, a halogenated hydrocarbon, such as methylene chloride, chlorobenzene or dichlorobenzene, an ester, such as ethyl acetate, and the like, at temperatures of between approximately room temperature and approximately 65° C.

In a preferred embodiment of the process, a compound of the formula (XIII) is used as starting material and is ozonised as indicated and then cleaved by reduction to form an oxalylazetidinone of the formula (XIV) which is reacted further, without being isolated from the reaction mixture, to form an azetidinone of the formula (VIb).

In the ozonolysis there may be produced small amounts of acid which can effect the removal of a radical $R_2$ that can readily be removed by solvolysis, for example a trisubstituted silyl radical. The resulting compound of the formula

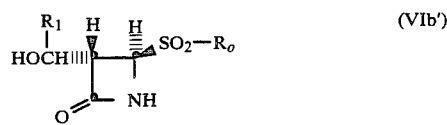

(VIb')

can be separated from the protected azetidinone (VIb), for example by chromatography, and converted into the azetidinone of the formula (VIb) by fresh reaction with the agent of the formula $R_2'$—$X_3$ that introduces the hydroxy-protecting group $R_2'$.

In the compounds of the formulae (II), (II'), (III), (IV), (VII) to (IX) and (XII) to (XIV), a protected carboxy group $R_3'$ can be converted into a different protected carboxy group $R_3'$ according to methods known per se, and when so doing it is possible, taking into consideration the other functional groups which may be contained in these compounds, to use the same methods as those indicated for the conversion of this substituent in the compounds of the formula (I).

The invention relates also to novel starting materials and to novel intermediates obtainable according to the process, such as those of the formulae (II) to (IX), (XIII) and (XIV) and to the processes given for their manufacture.

The starting materials used and the reaction conditions chosen are preferably those which result in the compounds described hereinbefore as being especially preferred.

The compounds of the formula I have valuable pharmacological properties, or can be used as intermediates for the manufacture of such compounds having valuable pharmacological properties. Compounds of the formula I in which $R_1$ represents hydrogen or methyl, $R_2$ represents hydroxy, $R_3$ represents carboxy, or an esterified carboxy group that can be cleaved under physiological conditions, and $R_4$ has the meaning given under formula I, and pharmacologically acceptable salts of such compounds having salt-forming groups have anti-bacterial activity. For example, they are effective in vitro against gram-positive and gram-negative cocci, for example *Staphylococcus aureus, Streptococcus pyogenes, Streptococcus pneumoniae,* and *Streptococcus faecalis,* and against gram-negative rod-shaped bacilli, such as *Enterobacteriaceae, Haemophilus influenzae* and *Pseudomonas aeruginosa,* and anaerobes, for example *Bacteroides sp.,* in minimum concentrations of from approximately 0.02 to approximately 64 μg/ml. In vivo, in the case of systemic infection of mice, for example by

*Staphylococcus aureus* or *Streptococcus pyogenes*, on subcutaneous or oral administration of compounds of the invention $ED_{50}$ values of from approximately 8.5 to approximately 100 mg/kg result.

For example, in vitro, sodium (5R,6S)-2-[3-(1-methyltetrazol-5-ylthio)-propyl]-6-hydroxymethyl-2-penem-3-carboxylate (compound 1) and sodium (5R,6S)-2-[3-(1-dimethylaminoethyltetrazol-5-ylthio)-propyl]-6-hydroxymethyl-2-penem-3-carboxylate (compound 2) and sodium (5R,6S)-2-[3-(1-methyltetrazol-5-ylthio)-ethyl-6-hydroxymethyl-2-penem-3-carboxylate (compound 3), have the following activity:

| Microorganism | MIC (μg/ml), in vitro | | |
|---|---|---|---|
| Compound | 1 | 2 | 3 |
| *Staphylococcus aureus* 10 B | 0.05 | 0.2 | 0.05 |
| *Staphylococcus aureus* 2999i+p+ | 0.05 | 0.2 | 0.05 |
| *Staphylococcus aureus* A 124 | | | 0.5 |
| *Staphylococcus aureus* Wood 46 | | | 0.05 |
| *Streptococcus pyogenes* Aronson | 0.1 | 0.1 | 0.1 |
| *Streptococcus pneumoniae* III/84 | 0.02 | 0.1 | 0.02 |
| *Streptococcus faecalis* D 3 | 64 | 32 | 32 |
| *Neisseria meningitidis* 1316 | | 0.05 | 0.02 |
| *Neisseria gonorrhoeae* 1317-4 | | 0.02 | 0.01 |
| *Haemophilus influenzae* NCTC 4560 | 0.5 | 2 | 2 |
| *Escherichia coli* 205 | 2 | 4 | 1 |
| *Escherichia coli* 205 R+TEM | 4 | 4 | 2 |
| *Escherichia coli* 16 | 16 | 8 | 4 |
| *Escherichia coli* 2018 | | | 0.5 |
| *Escherichia coli* UB 1005 | 4 | 4 | 2 |
| *Escherichia coli* DC 2 | 2 | 2 | 2 |
| *Escherichia coli* B-1385 | | | 2 |
| *Klebsiella pneumoniae* 327 | 4 | 4 | 2 |
| *Serratia marcescens* 344 | 16 | 16 | 16 |
| *Enterobacter cloacae* P 99 | 32 | 16 | 16 |
| *Enterobacter cloacae* ATCC 13047 | 64 | >32 | 32 |
| *Proteus mirabilis* 774 | 2 | 4 | 2 |
| *Proteus mirabilis* 1219 | 8 | 8 | 4 |
| *Proteus rettgeri* 856 | 4 | 16 | 4 |
| *Proteus morganii* 2359 | 2 | 4 | 2 |
| *Proteus morganii* 1518 | 4 | 8 | 4 |
| *Pseudomonas aeruginosa* ATCC 12055 | >128 | >32 | >128 |
| *Pseudomonas aeruginosa* K 799/61 | 2 | 8 | 1 |
| *Clostridium perfringens* 194 | 0.02 | 0.1 | 0.1 |
| *Bacteroides fragilis* L 01 | 0.5 | 1 | 0.2 |

In vivo in the systemic infection of mice, the following activity is found:

| | $ED_{50}$ (mg/kg) in vivo | | | | | |
|---|---|---|---|---|---|---|
| Compound | 1 | | 2 | | 3 | |
| Microorganism | s.c. | p.o. | s.c. | p.o. | s.c. | p.o. |
| *Staphylococcus aureus* 10 B | 60 | 90 | n.d. | n.d. | n.d. | n.d. |
| *Streptococcus pyogenes* Aronson | 8.5 | approx. 30 | >3 | >3 | 12 | 30 |
| *Escherichia coli* 2018 | 30–100 | 90 | n.d. | n.d. | n.d. | n.d. |

(s.c.: subcutaneous; p.o.: peroral; n.d.: not determined)

The novel compounds can be used as oral or parenterally administrable antibacterial antibiotics, for example in the form of corresponding pharmaceutical preparations, for the treatment of infections.

Compounds of the formula I in which at least one of the functional groups present is in protected form, a protected carboxy group being other than an esterified carboxy group that can be cleaved under physiological conditions, can be used as intermediates for the manufacture of the above-mentioned pharmacologically active compounds of the formula I.

The pharmacologically acceptable compounds of the present invention can be used, for example, for the manufacture of pharmaceutical preparations that contain an effective amount of the active ingredient together or in admixture with inorganic or organic, solid or liquid, pharmaceutically acceptable carriers that are suitable for oral or for parenteral, that is to say intramuscular, subcutaneous or intraperitoneal, administration.

For oral administration there are used tablets or gelatine capsules that contain the active ingredient together with diluents, for example lactose, dextrose, sucrose, mannitol, sorbitol, cellulose and/or glycine, and lubricants, for example silica, talc, stearic acid or salts thereof, such as magnesium or calcium stearate, and/or polyethylene glycol; tablets also contain binders, for example magnesium aluminium silicate, starches, such as maize, wheat, rice or arrowroot starch, gelatine, tragacanth, methylcellulose, sodium carboxymethylcellulose and/or polyvinylpyrrolidone, and, if desired, disintegrators, for example starches, agar, alginic acid or a salt thereof, such as sodium alginate, and/or effervescent mixtures or adsorbents, colourings, flavourings or sweeteners.

For parenteral administration there are suitable especially infusion solutions, preferably isotonic aqueous solutions or suspensions, it being possible to prepare these before use, for example from lyophilised preparations that contain the active ingredient alone or together with a carrier, for example mannitol. Such preparations may be sterilised and/or contain adjuncts, for example preservatives, stabilisers, wetting agents and/or emulsifiers, solubilisers, salts for regulating the osmotic pressure and/or buffers.

The present pharmaceutical preparations, which, if desired, may contain other pharmacologically active substances, are manufactured in a manner known per se, for example by means of conventional mixing, dissolving or lyophilising processes, and contain from approximately 0.1 to 100%, especially from approximately 1 to approximately 50% or, in the case of lyophilisates, up to 100%, of the active ingredient.

Depending upon the type of infection and the condition of the infected organism, the daily dose to be administered for the treatment of a warm-blooded animal (human or animal) weighing approximately 70 kg is from approximately 0.1 g to approximately 5 g.

The following Examples serve to illustrate the invention. Temperatures are given in degrees Centigrade. The following abbreviations are used in the Examples:

TLC: thin-layer chromatograph
IR: infra-red spectrum
UV: ultraviolet spectrum
M.p.: melting point
DBU: 1,5-diazabicyclo[5.4.0]undec-5-ene
THF: tetrahydrofuran
DMF: dimethylformamide

Experimental section

EXAMPLE 1

(3S,4R)-3-(tert.Butyl-dimethylsilyloxymethyl)-4-[4-(1-methyltetrazol-5-ylthio)butyroylthio]-azetidin-2-one While stirring at room temperature, a mixture of 720 mg of 4-(1-methyltetrazol-5-ylthio)-thiobutyric acid, 3.3 ml of 1N sodium hydroxide solution and 6.9 ml of water is added dropwise to a solution of 880.2 mg of (3S,4R)-3-(tert.-butyl-dimethyl-silyloxymethyl)-4-methylsulphonylazetidin-2-one in 6 ml of absolute THF. Sodium hydroxide solution is then metered in in such a manner that the pH is between 9 and 10. After a reaction time of 3.5 hours at room temperature, the whole is extracted with methylene chloride. The organic extracts are washed with brine, dried over sodium sulphate and concentrated by evaporation. The crude product is chromatographed over 50 g of silica gel with the eluant toluene and ethyl acetate 2:1.

TLC (silica gel): toluene/ethyl acetate (2:3) $R_f$=0.45.
IR (methylene chloride): 2.93; 5.67; 5.96μ.

The starting compound 4-(1-methyltetrazol-5-ylthio)-thiobutyric acid can be produced as follows:

(1aa) 4-(1-Methyltetrazol-5-ylthio)-butyric acid ethyl ester 5.34 g of sodium (1-methyltetrazol-5-ylthiolate) and 6.44 g of 4-bromobutyric acid ethyl ester are stirred for 3 hours at 90° in 60 ml of absolute ethanol. The reaction mixture is then concentrated by evaporation and the resulting residue is partitioned between water and ethyl acetate. The organic phase is dried over sodium sulphate and concentrated by evaporation under reduced pressure to give the title compound.

TLC (eluant toluene/ethyl acetate 1:1): $R_f$=0.4.
IR (methylene chloride): 5.78; 7.3; 8.62μ.

(1ab) 4-(1-Methyltetrazol-5-ylthio)-butyric acid 2.93 g of 4-(1-methyltetrazol-5-ylthio)-butyric acid ethyl ester are dissolved in 50 ml of THF, 15 ml of 1N NaOH are added and the whole is stirred for 3 hours at room temperature. Most of the THF is then concentrated by evaporation under reduced pressure in a rotary evaporator and the residue is washed with ethyl acetate. The aqueous solution is adjusted to pH 3 with 4N HCl and extracted three times with ethyl acetate. After drying over sodium sulphate and concentration by evaporation under reduced pressure, the pure title compound is obtained.

TLC (eluant: toluene/ethyl acetate/acetic acid: 10:10:1): $R_f$=0.29.
IR (methylene chloride): 5.87; 7.2; 8.55μ.

(1ac) 4-(1-Methyltetrazol-5-ylthio)-butyric acid chloride 2.2 g of 4-(1-methyltetrazol-5-ylthio)-butyric acid are stirred in 20 ml of absolute benzene with 1.03 ml of thionyl chloride and 4 drops of DMF for 20 minutes at the reflux temperature. The solvent is then concentrated by evaporation under reduced pressure. After dissolving and concentrating by evaporation twice more in toluene, the pure title compound is obtained in the form of a yellow oil.

IR (methylene chloride): 5.6; 7.2; 8.6μ.

(1ad) 4-(1-Methyltetrazol-5-ylthio)-thiobutyric acid 920 mg of 4-(1-methyltetrazol-5-ylthio)-butyric acid chloride are dissoved in 1.4 ml of absolute methylene chloride and added dropwise at 0° to 5.54 ml of a pyridine/H₂S solution in methylene chloride (30 ml of absolute pyridine and 6 g of H₂S in 100 ml of methylene chloride). The whole is then stirred for one hour at 0° under a nitrogen atmosphere. The reaction mixture is taken up in chloroform, the aqueous phase is acidified to a pH of 2 using 2N H₂SO₄ and extraction is carried out twice with chloroform. The combined organic phases are washed twice with 5 ml of 10% NaHCO₃ solution. The pH is then adjusted to 3 using 2N H₂SO₄ and the title compound is extracted several times with chloroform. The title compound is obtained after drying over sodium sulphate and concentrating.

IR (methylene chloride): 3.9; 5.9; 7.1; 7.2; 8.55μ.

The starting material (3S,4R)-3-(tert.-butyldimethylsilyloxymethyl)-4-methylsulphonylazetidin-2-one can be produced as follows:

(1ba) (3S,5R,6R)-2,2-Dimethyl-6-(tert.-butyl-dimethylsilyloxymethyl)-penam-3-carboxylic acid methyl ester 1,1-dioxide A solution of 23.6 g (85 mmol) of (3S,5R, 6R)-2,2-dimethyl-6-hydroxymethylpenam-3-carboxylic acid methyl ester 1,1-dioxide in 50 ml of dimethylformamide is stirred at room temperature for 45 minutes with 25.5 g (170 mmol) of tert.-butyldimethylchlorosilane and 11.5 g (170 mmol) of imidazole. The solvent is then distilled off in a high vacuum and the residue is taken up in ethyl acetate. The solution is washed with 1N sulphuric acid and then with water, and the aqueous solutions are extracted twice with ethyl acetate. The organic phase is dried with sodium sulphate and concentrated in a rotary evaporator. The product is obtained in the form of a crystalline mass.

TLC silica gel, toluene/ethyl acetate (4:1): $R_f$=0.56.
IR (CH₂Cl₂) 3.4; 5.57; 5.65 μm.

(1bb) 2-[(3S,4R)-3-(tert.-Butyl-dimethyl-silyloxymethyl)-4-methylsulphonyl-2-oxoazetidin-1-yl]-3-methyl-2-butenoic acid methyl ester 9 ml of DBU are added to a solution of 202 g (0.51 mol) of (3R,5R,6R)-2,2-dimethyl-6-(tert.-butyl-dimethyl-silyloxymethyl)-penam-3-carboxylic acid methyl ester 1,1-dioxide in 800 ml of tetrahydrofuran and the whole is stirred at room temperature for 5 minutes. Then a further 95 ml of DBU are added and the whole is stirred at room temperature for 30 minutes. Subsequently, 42.3 ml (0.68 mol) of methyl iodide are added while cooling. After a reaction time of 3 hours, the DBU-hydriodide which has crystallised is filtered off and the filtrate is concentrated. The residue is taken up in ethyl acetate and the solution is washed with 1N sulphuric acid, water and bicarbonate solution. The aqueous phases are extracted twice with ethyl acetate. The combined organic phases are dried over sodium sulphate and the solution is concentrated to a thick oil.

TLC [silica gel, toluene/ethyl acetate (4:1)]: $R_f$=0.42.
IR (CH₂Cl₂) 5.63; 5.81; 6.17 μm.

(1bc)
(3S,4R)-3-Hydroxymethyl-4-methylsulphonylazetidin-2-one and
(3S,4R)-3-(tert.-butyl-dimethyl-silyloxymethyl)-4-methylsulphonylazetidin-2-one A solution of 25 g (61.7 mmol) of 2-[(3S,4R)-3-(tert.-butyl-dimethyl-silyloxymethyl)-4-methylsulphonyl-2-oxoazetidin-1-yl]-3-methyl-2-butenoic acid methyl ester in 400 ml of methylene chloride is treated at −10° with an ozone/oxygen mixture. The disappearance of the starting material is monitored by thin layer chromatography. When the reaction is complete, 30 ml of dimethyl sulphide are added and the whole is stirred for a further 3 hours at room temperature. The solution is concentrated and the residue is taken up in a mixture of 160 ml of methanol, 24 ml of ethyl acetate and 3 ml of water and heated for 40 minutes at 70°. The solvent is then removed and the residue is evaporated twice in the presence of toluene. The crystallising oil is taken up in methylene chloride and the crystals, consisting of (3S,4R)-3-hydroxymethyl-4-methylsulphonylazetidin-2-one, are isolated by filtration. The filtrate is concentrated and (3S,4R)-3-(tert.-butyl-dimethyl-silyloxymethyl)-4-methylsulphonylazetidin-2-one is obtained in pure form by chromatography over silica gel with toluene/ethyl acetate (3:1).

(3S,4R)-3-hydroxymethyl-4-methylsulphonylazetidin-2-one

TLC, silica gel, toluene/ethyl acetate (1:1): $R_f=0.36$.
IR ($CH_2Cl_2$) 2.96, 3.54, 5.61 μm.

(3S,4R)-3-(tert.-butyl-dimethyl-silyloxymethyl)-4-methyl-sulphonylazetidin-2-one TLC, silica gel, toluene/ethyl acetate (1:1): $R_f=0.06$.
24 g (183 mmol) of tert.-butyldimethylchlorosilane and 11 g (163 mmol) of imidazole are added in the course of 45 minutes at room temperature to a solution of 14.6 g (81.5 mmol) of (3S,4R)-3-hydroxymethyl-4-methylsulphonylazetidin-2-one in 40 ml of dimethylformamide. The solvent is then removed in a high vacuum and the residue is taken up in ethyl acetate. The organic phase is washed in succession with 1N sulphuric acid, water and sodium bicarbonate solution. The aqueous phases are extracted twice with ethyl acetate. The combined organic phases are dried over sodium sulphate and concentrated in a rotary evaporator. The crystalline residue is pure (3S, 4R)-3-(tert.-butyl-dimethyl-silyloxymethyl)-4-methylsulphonylazetidin-2-one.

EXAMPLE 2

2-[(3S,4R)-3-(tert.-Butyl-dimethyl-silyloxymethyl)-4-[4-(1-methyltetrazol-5-ylthio)-butyroylthio]-2-oxoazetidin-1-yl]-2-hydroxyacetic acid 2-trimethylsilyl ethyl ester 30 g of molecular sieve type 4 Å 1/16 (produced by Dr. Bender & Dr. Hobein AG, Zurich) are added to a mixture of 3.346 g of (3S,4R)-3-(tert.-butyl-dimethyl-silyloxymethyl)-4-[4-(1-methyltetrazol-5-ylthio)-butyroylthio]-azetidin-2-one and 3.417 g of glyoxylic acid 2-trimethylsilyl ethyl ester-ethyl hemiketal in 60 ml of toluene and 12 ml of N,N-dimethylformamide, and the whole is stirred for 8 hours at a bath temperature of 100° under a protective gas. After cooling, the mixture is filtered over Hyflo and the residue from filtration is washed with toluene. Concentration by evaporation of the filtrate and drying at 40° in a high vacuum yields the product in the form of a yellow oil.

TLC (silica gel): toluene/ethyl acetate (2:3) $R_f=0.55$ and 0.47.
IR (methylene chloride): 2.87; 5.65; 5.78; 5.93μ.

EXAMPLE 3

2-[(3S,4R)-3-(tert.-Butyl-dimethyl-silyloxymethyl)-4-[4-(1-methyltetrazol-5-ylthio)-butyroylthio]-2-oxoazetidin-1-yl-2-triphenylphosphoranylideneacetic acid 2-trimethylsilyl ethyl ester 1.04 ml of thionyl chloride and 2.08 ml of triethylamine are added in succession, in the course of 10 minutes, while stirring at −15°, to a solution of 5.2 g of 2-[(3S,4R)-3-(tert.-butyl-dimethyl-silyloxymethyl)-4-[4-(1-methyltetrazol-5-ylthio)-butyroylthio]-2-oxoazetidin-1-yl]-2-hyroxyacetic acid 2-trimethylsilyl ethyl ester in 35 ml of tetrahydrofuran. The white suspension is then stirred for 1 hour at 0° and filtered over Hyflo. After washing the residue with toluene, it is concentrated in a rotary evaporator and dried in a high vacuum. The residue is dissolved in 20 ml of dioxan, 2.25 g of triphenylphosphine and 1 ml of 2,6-lutidine are added and the whole is stirred for 18 hours at 50°. The mixture is filtered over Hyflo, and this residue is washed with toluene. The combined filtrates are concentrated by evaporation and chromatography of the residue over 300 g of silica gel with toluene/ethyl acetate (4:1) yields the pure product.

TLC (silica gel) toluene/ethyl acetate (2:3): $R_f=0.49$.
IR (methylene chloride): 5.7; 5.93; 6.25μ.

EXAMPLE 4

(5R,6S)-2-[3-(1-Methyltetrazol-5-ylthio)-propyl]-6-(tert.-butyl-dimethyl-silyloxymethyl-2-penem-3-carboxylic acid 2-trimethylsilyl ethyl ester 2.16 g of 2-[(3S,4R)-3-(tert.-butyl-dimethyl-silyloxymethyl)-4-[4-(1-methyltetrazol-5-ylthio)butyroylthio]-2-oxoazetidin-1-yl]-2-triphenylphosphoranylideneacetic acid 2-trimethylsilyl ethyl ester are dissolved in 800 ml of toluene and stirred at reflux temperature for 1.5 hours under a nitrogen atmosphere. Concentration by evaporation of the solvent and chromatography of the residue over silica gel with the eluant toluene/ethyl acetate (5:1) yields the pure product.

TLC (silica gel): toluene/ethyl acetate (2:3) $R_f=0.6$.
IR (methylene chloride): 5.63; 5.92; 6.35; 7.67; 8.95μ.

EXAMPLE 5

(5R,6S)-2-[3-(1-Methyltetrazol-5-ylthio)-propyl]-6-hydroxymethyl-2-penem-3-carboxylic acid 2-trimethylsilyl ethyl ester 1 g of (5R,6S)-2-[3-(1-methyltetrazol-5-ylthio)-propyl]-6-tert.-butyl-dimethyl-silyloxymethyl)-2-penem-3-carboxylic acid 2-trimethylsilyl ethyl ester is dissolved in 28 ml of absolute THF and, under a nitrogen atmosphere, after cooling to −80°, 1 ml of acetic acid is added. 80 ml of a 0.1M tetrabutylammonium fluoride solution in THF are then added dropwise and the mixture is allowed to rise to room temperature and is stirred for 2 hours at that temperature. The volume of solvent is concentrated to 5 ml in a rotary evaporator and the residue is partitioned between 147 mg of sodium bicarbonate in 50 ml of water and 50 ml of ethyl acetate. The organic phase is separated off, and the aqueous phase is extracted twice more with ethyl acetate. The organic extracts are washed once more with water and dried over sodium sulphate. Concentration by evaporation in a high vacuum yields the crude product, which is chromatographed over 40 g of silica gel with the eluant toluene/ethyl acetate (1:1).

TLC (silica gel) toluene/ethyl acetate (2:3): $R_f=0.2$.
IR (methylene chloride): 2.78; 5.63; 5.92; 6.35; 7.67μ.

EXAMPLE 6

Sodium (5R,6S)-2-[3-(1-methyltetrazol-5-ylthio)-propyl]-6-hydroxymethyl-2-penem-3-carboxylate 770 mg of (5R,6S)-2-[3-(1-methyltetrazol-5-ylthio)-propyl]-6-hydroxymethyl-2-penem-3-carboxylic acid 2-trimethylsilyl ethyl ester are dissolved in 14 ml of absolute THF and cooled to −30°. After the addition of 67.3 ml of 0.1M tetrabutylammonium fluoride solution in THF, the temperature is increased to 0°. After stirring for 10 minutes at this temperature, 90 ml of ethyl acetate and 90 ml of water are added to the mixture. The solution is then adjusted to pH 3 by the dropwise addition of 4N HCl in an ice bath. The aqueous phase is subsequently separated off and the ethyl acetate phase is extracted with 71 ml of 0.05M NaHCO₃ solution. The organic phase is extracted once more with 10 ml of NaHCO₃ (0.05M) and 10 ml of H₂O. The combined aqueous phases are in vacuo freed of remaining solvent and lyophilised.

TLC (reversed phase Opti-UPC$_{12}$): acetonitrile/water (1:1) $R_f=0.78$.
UV (phosphate buffer pH 7.4): $\lambda_{max}=303$ nm.

EXAMPLE 7

(3S,4R)-3-[(1R)-1-tert.-Butyl-dimethyl-silyloxyethyl]-4-[4-(1-methyltetrazol-5-ylthio)-butyroylthio]-azetidin-2-one The title compound is produced analogously to Example 1, using as the starting material 921 mg of (3S,4R)-3-[(1R)-1-tert.-butyl-dimethyl-silyloxyethyl]-4-methylsulphonylazetidin-2-one and 720 mg of 4-(1-methyltetrazol-5-ylthio)-thiobutyric acid.

IR (methylene chloride): 2.9; 5.65; 5.95μ.

The starting compound (3S,4R)-3-[(1R)-1-tert.-butyl-dimethyl-silyloxyethyl]-4-methylsulphonylazetidin-2-one can be produced as follows:

In a manner analogous to that described in Examples (1ba) to (1bc), by reaction of (3S,5R,6R)-2,2-dimethyl-6-[(1R)-1-hydroxyethyl]-penam-3-carboxylic acid benzyl ester 1,1-dioxide (German Offenlegungsschrift No. 3039504) with tert.-butyldimethylchlorosilane and imidazole, (3S,5R,6R)-2,2-dimethyl-6-[(1R)-1-(tert.-butyl-dimethyl-silyloxy)-ethyl]-penam-3-carboxylic acid benzyl ester 1,1-dioxide [IR (methylene chloride): 3.42; 5.56; 5.63μ] is obtained, which is treated with DBU and then with DBU/methyl iodide. The resulting 2-[(3S,4R)-3-((1R)-1-(tert.-butyl-dimethyl-silyloxy)-ethyl)-4-methylsulphonyl-2-oxoazetidin-1-yl]-3-methyl-2-butenoic acid benzyl ester [IR (methylene chloride): 5.63; 5.80; 6.15μ] yields the desired product when ozonolised and subsequently treated with methanol.

EXAMPLE 8

2-[(3S,4R)-3-((1R)-1-tert.-Butyl-dimethyl-silyloxyethyl)-4-[4-(1-methyltetrazol-5-ylthio)-butyroylthio]-2-oxoazetidin-1-yl]-2-hydroxyacetic acid 2-trimethylsilyl ethyl ester The title compound is manufactured analogously to Example 2, using as the starting material 3.45 g of (3S,4R)-3-((1R)-1-tert.-butyl-dimethyl-silyloxyethyl)-4-[4-(1-methyltetrazol-5-ylthio)-butyroylthio]azetidin-2-one and 3.42 g of glyoxylic acid 2-trimethylsilyl ethyl ester-ethyl hemiketal.

IR (methylene chloride): 2.85; 5.66; 5.76; 4.96μ.

EXAMPLE 9

2-[3S,4R)-3-((1R)-1-tert.-Butyl-dimethyl-silyloxyethyl)-4-[4-(1-methyltetrazol-5-ylthio)-butyroylthio]-2-oxoazetidin-1-yl]-2-triphenylphosphoranylideneacetic acid 2-trimethylsilyl ethyl ester Analogously to Example 3, 5.28 g of 2-[(3S,4R)-3-((1R)-1-tert.-butyl-dimethyl-silyloxyethyl)-4-[4-(1-methyltetrazol-5-ylthio)-butyroylthio]-2-oxoazetidin-1-yl]-2-hydroxyacetic acid 2-trimethylsilyl ethyl ester are converted into the title compound.

IR (methylene chloride): 5.73; 5.91; 6.23μ.

EXAMPLE 10

(5R,6S)-2-[3-(1-Methyltetrazol-5-ylthio)-propyl]-6-[(1R)-1-tert.-butyl-dimethyl-silyoxyethyl]-2-penem-3-carboxylic acid 2-trimethylsilyl ethyl ester Analogously to Example 4, 2.27 g of 2-[(3S,4R)-3-((1R)-1-tert.-butyl-dimethyl-silyloxyethyl)-4-[4-(1-methlytetrazol-5-ylthio)-butyroylthio]-2-oxoazetidin-1-yl]-2-triphenylphosphoranylideneacetic acid 2-trimethylsilyl ethyl ester are cyclised to form the title compound.

IR (methylene chloride): 5.60; 5.90; 6.32; 7.63; 8.95μ.

EXAMPLE 11

(5R,6S)-2-[3-(1-Methyltetrazol-5-ylthio)-propyl]-6-[(1R)-1-hydroxyethyl]-2-penem-3-carboxylic acid 2-trimethylsilyl ethyl ester Analogously to Example 5, 1.02 g of (5R,6S)-2-[3-(1-methyltetrazol-5-ylthio)-propyl]-6-[(1R)-1-tert.-butyl-dimethyl-silyloxyethyl]-2-penem-3-carboxylic acid 2-trimethylsilyl ethyl ester are reacted after being stirred for 100 hours at room temperature with 80 ml of a 0.1M tetrabutylammonium fluoride solution in THF and 1 ml of acetic acid to form the title compound.

IR (methylene chloride): 2.81; 5.62; 5.94; 6.33; 7.67μ.

EXAMPLE 12

Sodium (5R,6S)-2-[3-(1-methyltetrazol-5-ylthio)-propyl]-6-[(1R)-1-hydroxyethyl]-2-penem-3-carboxylate Analogously to Example 6, 0.7 g of (5R,6S)-2-[3-(1-methyltetrazol-5-ylthio)-propyl]-6-[(1R)-1-hydroxyethyl]-2-penem-3-carboxylic acid 2-trimethylsilyl ethyl ester is reacted to form the title compound.

UV (phosphate buffer pH 7.4) $\lambda_{max}=305$ nm.

EXAMPLE 13

(3S,4R)-3-(tert.-Butyl-dimethyl-silyloxymethyl)-4-triphenylmethylthioazetidin-2-one 12.5 g of triphenylmethylmercaptan are suspended at 0° in 70 ml of methanol and in the course of 10 minutes a total of 2.2 g of a 50% sodium hydride suspension in oil is added in portions. Subsequently an emulsion of 11.1 g of 3-tert.-butyl-dimethylsilyloxymethyl-4-methylsulphonylazetidin-2-one in 70 ml of acetone and 70 ml of water is added dropwise in the course of 30 minutes. After stirring for 30 minutes at 0° and for 1 hour at room temperature, the reaction mixture is concentrated in a rotary evaporator, methylene chloride is added thereto and the aqueous phase is separated off. The organic solution is washed with brine and dried over sodium sulphate. After concentration the crude title compound is purified by chromatography over silica gel (eluant toluene/ethyl acetate 19:1).

TLC (toluene/ethyl acetate 19:1): $R_f=0.64$.
IR (methylene chloride): 2.95; 5.68; 8.95; 12μ.

EXAMPLE 14

2-[(3S,4R)-3-(tert.-Butyl-dimethyl-silyloxymethyl)-4-triphenylmethylthio-2-oxoazetidin-1-yl]-2-hydroxyacetic acid 2-trimethylsilyl ethyl ester.

1.34 g of (3S,4R)-3-(tert.-butyl-dimethyl-silyloxymethyl)-4-triphenylmethylthioazetidin-2-one and 0.887 g of glyoxylic acid 2-trimethylsilyl ethyl ester-ethyl hemiketal in 50 ml of absolute toluene are heated for 18 hours under reflux on a water separator (which has been filled with 4 Å molecular sieve) under nitrogen. After concentration in a rotary evaporator under reduced pressure the crude product is purified by chromatography over silica gel.

TLC (eluant toluene/ethyl acetate 1:1): $R_f=0.67$.
IR (methylene chloride) 2.85; 5.67; 5.78; 11.8μ.

EXAMPLE 15

2-[3S,4R)-3-(tert.-Butyl-dimethyl-silyloxymethyl)-4-triphenylmethylthio-2-oxoazetidin-1-yl]-2-triphenyl-phosphoranylideneacetic acid-2-trimethylsilyl ethyl ester Analogously to Example 3, 1.15 g of 2-[(3S,4R)-3-(tert.-butyl-dimethyl-silyloxymethyl)-4-triphenylmethylthio-2-oxoazetidin-1-yl]-2-hydroxyacetic acid 2-trimethylsilyl ethyl ester are converted into the title compound.

IR (methylene chloride) 5.75; 6.23; 9.05; 11.9μ.

EXAMPLE 16

2-[(3S,4R)-3-Hydroxymethyl-4-triphenylmethylthio-2-oxoazetidin-1-yl]2-triphenylphosphoranylideneacetic acid 2-trimethylsilyl ethyl ester 454 mg of 2-[(3S,4R)-3-(tert.-butyl-dimethylsilyloxymethyl)-4-triphenylmethylthio-2-oxoazetidin-1-yl]-2-triphenylphosphoranylideneacetic acid 2-trimethylsilyl ethyl ester are dissolved in 6 ml of absolute THF and 0.2 ml of acetic acid is added dropwise thereto at −78°. Subsequently 15 ml of a 0.1M tetrabutylammonium fluoride (TBAF) solution in THF is added dropwise thereto. The mixture is then allowed to rise to room temperature while stirring; after 1¾ hours a further 315 mg of TBAF and after 17 hours a further 315 mg are added thereto. After 41 hours at room temperature the whole is diluted with 150 ml of methylene chloride and washed once with 50 ml of a saturated $NaHCOR_3$ solution and then with 50 ml of brine. After drying over magnesium sulphate and concentration by evaporation, the crude title compound is purified by chromatography over silica gel (eluant: ethyl acetate).

TLC (silica gel; eluant: ethyl acetate): $R_f=0.46$.
IR (methylene chloride) 2.7; 5.78; 6.23; 9.05μ.

EXAMPLE 17

Silver salt of 2-[(3S,4R)-3-hydroxymethyl-4-mercapto-2-oxoazetidin-1-yl]-2-triphenylphosphoranylideneacetic acid 2-trimethylsilyl ethyl ester 0.29 g of 2-[(3S,4R)-3-hydroxymethyl-4-triphenylmethylthio-2-oxoazetidin-1-yl]-2-triphenylphosphoranylideneacetic acid 2-trimethylsilyl ethyl ester is dissolved in 4 ml of ether and at room temperature 2.9 ml of a 0.5M aqueous silver nitrate solution are added. The resulting beige-coloured suspension is then treated with 0.84 ml of a mixture of 0.36 ml of tributylamine, 0.018 ml of triluoroacetic acid and 2.4 ml of ether. After stirring for 20 minutes at room temperature the solid substance is filtered off, washed with ether and water, and again with ether, and dried in a high vacuum.

IR (methylene chloride) 2.95; 5.7; 6.2; 9.05μ.

EXAMPLE 18

2-[(3S,4R)-3-Hydroxymethyl-4-[4-(1-dimethylaminoethyltetrazol-5-ylthio)-butyroylthio]-2-oxoazetidin-1-yl]-2-triphenylphosphoranylideneacetic acid 2-trimethylsilyl ethyl ester 1.2 ml of triethylamine, 1.09 ml of trimethylchlorosilane and 50 mg of imidazole are added at −25° to a solution of 1.41 g (2.14 mmol) of the silver salt of 2-[(3S,4R)-3-hydroxymethyl-4-mercapto-2-oxoazetidin-1-yl]-2-triphenylphosphoranylideneacetic acid 2-trimethylsilyl ethyl ester in 25 ml of absolute THF. After stirring for 30 minutes at −25°, the cooling bath is removed and the whole is stirred for a further 16 hours. The mixture is cooled to 0°, diluted with 28 ml of methylene chloride and treated in succession with 0.365 ml of pyridine and with a solution of 603.5 mg of 4-chlorobutyric acid chloride in 5 ml of methylene chloride. The reaction mixture is stirred for one hour at 0°, then filtered over Hyflo and carefully concentrated in a high vacuum at room temperature. The residue is dissolved in 6 ml of DMSO, and 742 mg of 1-(N,N-dimethylaminoethyl)-tetrazol-5-thiol and 0.6 ml of triethylamine are added thereto. After stirring for 140 hours at room temperature, 200 ml of ethyl acetate and 120 ml of water are added and the whole is rendered basic with saturated sodium bicarbonate solution. The organic phase is dried over $MgSO_4$ and concentrated. The residue is dissolved in 40 ml of methylene chloride and treated with 2 ml of water and 0.1 ml of trifluoroacetic acid. After stirring for 1.5 hours at room temperature, the organic solution is washed with aqueous $NaHCO_3$ solution and $H_2O$, dried over $Na_2SO_4$ and concentrated by evaporation. The crude title compound is purified by chromatography over silica gel.

IR (methylene chloride) 2.78; 5.75; 5.95; 6.25μ.

EXAMPLE 19

(5R,6S)-2-[3-(1-Dimethylaminoethyltetrazol-5-ylthio)-propyl]-6-hydroxymethyl-2-penem-3-carboxylic acid 2-trimethylsilyl ethyl ester Analogously to Example 4, 3 g of 2-[(3S,4R)-3-hydroxymethyl-4-[4-(1-dimethylaminoethyltetrazol-5- ylthio)-butyroylthio]-2-oxoazetidin-1-yl]-2-triphenylphosphoranylideneacetic acid 2-trimethylsilyl ethyl ester are converted into the title compound by heating in toluene.

IR (methylene chloride) 2.76; 5.61; 5.9; 6.33µ.

EXAMPLE 20

Sodium (5R,6S)-2-[3-(1-dimethylaminoethyltetrazol-5-ylthio)-propyl]-6-hydroxymethyl-2-penem-3-carboxylate Analogously to Example 5, 0.5 g of (5R,6S)-2-[3-(1-dimethylaminoethyltetrazol-5-ylthio)-propyl]-6-hydroxymethyl-2-penem-3-carboxylic acid 2-trimethylsilyl ethyl ester is reacted to form the title compound.

UV (phosphate buffer pH 7.4) $\lambda^1_{max}$303 nm, $\lambda^2_{max}$237 nm.

EXAMPLE 21

2-[(3S,4R)-3-Hydroxymethyl-4-[4-(2-pyridylthio)-butyroylthio]-2-oxoazetidin-1-yl]-2-triphenylphosphoranylideneacetic acid 2-trimethylsilyl ethyl ester Analogously to Example 18, 1.41 g of the silver salt of 2-[(3S,4R)-3-hydroxymethyl-4-mercapto-2-oxoazetidin-1-yl]-2-triphenylphosphoranylideneacetic acid 2-trimethylsilyl ethyl ester are reacted with 603.5 mg of 4-chlorobutyric acid chloride and then with 475 mg of 2-pyridinethiol to form the title compound.

IR (methylene chloride): 2.76; 5.74; 5.95µ.

EXAMPLE 22

(5R,6S)-2-3-Pyrid-2-ylthio)-propyl]-6-hydroxymethyl-2-penem-3-carboxylic acid 2-trimethylsilyl ethyl ester Analogously to Example 4, 2 g of 2-[(3S,4R)-3-hydroxymethyl-4-[4-(2-pyridylthio)-butyroylthio]-2-oxoazetidin-1-yl]-2-triphenylphosphoranylideneacetic acid 2-trimethylsilyl ethyl ester are converted into the title compound by heating in toluene.

IR (methylene chloride): 2.77; 5.60; 5.93; 6.31µ.

EXAMPLE 23

Sodium (5R,6S)-2-[3-(pyrid-2-ylthio)-propyl]-6-hydroxymethyl-2-penem-3-carboxylate Analogously to Example 6, 0.4 g of (5R,6S)-2-[3-(pyrid-2-ylthio)-propyl]-6-hydroxymethyl-2-penem-3-carboxylic acid 2-trimethylsilyl ethyl ester is reacted to form the title compound.

UV (phosphate buffer): $\lambda_{max}$304 nm.

EXAMPLE 24

2-[(3S,4R)-3-(tert.-Butyl-dimethyl-silyloxymethyl)-4-[3-(1-methyltetrazol-5-ylthio)-propionylthio]-2-oxoazetidin-1-yl]-2-triphenylphosphoranylideneacetic acid allyl ester 4.5 g of the silver salt of 2-[(3S,4R)-3-(tert.-butyl-dimethyl-silyloxymethyl)-4-mercapto-2-oxoazetidin-1-yl]-2-triphenylphosphoranylideneacetic acid allyl ester in 100 ml of absolute methylene chloride are treated with 1.26 ml of pyridine and 20 mg of 4-dimethylaminopyridine and then at 0°, a solution of 3-(1-methyltetrazol-5-ylthio)-propionyl chloride is added dropwise. After stirring for 30 minutes the precipitated silver chloride is filtered off over Hyflo, the filtrate is diluted with methylene chloride and washed in succession with aqueous sodium bicarbonate solution and then with brine. After drying over Na$_2$SO$_4$, the whole is concentrated in vacuo. The residue is purified by chromatography over silica gel (eluant toluene/ethyl acetate 9:1 to 4:1).

IR (methylene chloride): 5.71; 5.93µ.

The starting compound 3-(1-methyltetrazol-5-ylthio)-propionyl chloride is produced as follows:

(24aa) 3-(1-Methyltetrazol-5-ylthio)-propionic acid ethyl ester 3.62 g of 3-bromopropionic acid ethyl ester are dissolved in 30 ml of ethanol and a solution of 3.56 g of sodium 1-methyltetrazol-5-ylthiolate in 35 ml of ethanol is added dropwise and the whole is then stirred for 18 hours under a protective gas. After concentration by evaporation of the ethanol, the residue is partitioned between water and ethyl acetate. The organic phase is separated off, dried and concentrated by evaporation. After chromatography over silica gel (eluant toluene-/ethyl acetate 10:1) the pure title compound is obtained.

IR (methylene chloride): 5.78; 7.30; 8.4µ.

(24ab) 3-(1-Methyltetrazol-5-ylthio)-propionic acid 5.43 g of 3-(1-methyltetrazol-5-ylthio)-propionic acid ethyl ester are dissolved in 20 ml of acetic acid, 4 ml of conc. HCl and 8 ml of water and the whole is stirred for 3.5 hours at 100°. After concentration of the reaction mixture by evaporation, the residue is partitioned between ethyl acetate and aqueous sodium bicarbonate solution. The aqueous phase is separated off, acidified with 4N HCl and extracted twice with ethyl acetate. After drying and concentration by evaporation the title compound is obtained.

NMR (DMSO-d$_6$): δ=2.8 (2H,t); 3.5 (4H,t); 4 ppm (3H,s).

(24ac) 3-(1-Methyltetrazol-5-ylthio)-propionyl chloride 1.46 g of 3-(1-methyltetrazol-5-ylthio)-propionic acid are suspended in 18 ml of absolute methylene chloride and 0.19 ml of 1-chloro-1-dimethylaminoisobutene is added. After stirring for 60 minutes under a protective gas, the crude acid chloride solution [IR: (methylene chloride): 5.59µ] is immediately reacted further (see above).

The starting material 2-[(3S,4R)-3-(tert.-butyl-dimethyl-silyloxymethyl)-4-mercapto-2-oxoazetidin-1-yl]-2-triphenylphosphoranylideneacetic acid allyl ester (silver salt) is produced as follows:

(24ba) 2-[(3S,4R)-3-(tert.-Butyl-dimethyl-silyloxymethyl)-4-triphenylmethylthio-2-oxoazetidin-1-yl]-2-hydroxyacetic acid allyl ester 27 g of molecular sieve (4 Å) are added to 8.4 g of (3S,4R)-3-(tert.-butyl-dimethyl-silyloxymethyl)-4-triphenylmethylthioazetidin-2-one (Example 13) and 8.23 g of glyoxylic acid allyl ester-ethyl hemiacetal in 170 ml of absolute toluene and the whole is stirred for 10 hours at 55°. After filtration and concentration in a rotary evaporator under reduced pressure, the crude product is purified by chromatography over silica gel. (Eluant toluene/ethyl acetate 95:5).

TLC (silica gel, toluene/ethyl acetate 10:1): R$_f$=0.37 and 0.27.

IR (CH$_2$Cl$_2$): 2.84; 5.68; 5.73µ.

(24 bb) 2-[(3S,4R)-3-(tert.-Butyl-dimethyl-silyloxymethyl)-4-triphenylmethylthio-2-oxoazetidin-1-yl]-2-triphenyl-phosphoranylideneacetic acid allyl ester While stirring at −15° 80 μl of thionyl chloride and 88 μl of pyridine are added in succession in the course of 5 minutes to a solution of 604 mg of 2-[(3S,4R)-3-(tert.-butyl-dimethyl-silyloxymethyl)-4-triphenylmethylthio-2-oxoazetidin-1-yl]-2-hydroxyacetic acid allyl ester in 5 ml of tetrahydrofuran. The white suspension is then stirred for one hour at −10° and filtered over Hyflo. After washing the residue with toluene concentration is effected in a rotary evaporator. The residue is dissolved in 3 ml of dioxan, 293 mg of triphenylphosphine and 0.13 ml of 2,6-lutidine are added and the whole is stirred for two hours at a bath temperature of 115°. The mixture is filtered over Hyflo and the residue is washed with toluene. The combined filtrates are concentrated by evaporation. Chromatography of the residue over silica gel yields the pure product (eluant toluene/ethyl acetate 95:5).

TLC (silica gel, toluene/ethyl acetate 1:1): $R_f$=0.18.
IR ($CH_2Cl_2$): 5.73; 6.23μ.

(24bc) Silver salt of 2-[(3S,4R)-3-(tert.-Butyl-dimethyl-silyloxymethyl)-4-mercapto-2-oxoazetidin-1-yl]-2-triphenylphosphoranylideneacetic acid allyl ester 7.5 g of 2-[(3S,4R)-3-(tert.-butyl-dimethyl-silyloxymethyl)-4-triphenylmethylthio-2-oxoazetidin-1-yl]-2-triphenylphosphoranylideneacetic acid allyl ester are introduced into 87 ml of ether and, at room temperature, 70 ml of a 0.5M aqueous silver nitrate solution are added. Subsequently, a mixture of 3.6 ml of tributylamine, 0.18 ml of trifluoroacetic acid and 25 ml of ether is added dropwise thereto and the reaction mixture is then stirred for 20 minutes. The solid substance is then filtered off with suction and washed with ether and water and again with ether. For purification, the solid substance is finally suspended again in 40 ml of ether and 40 ml of water, and the whole is filtered with suction and dried.

IR ($CH_2Cl_2$): 5.68; 6.17μ.

EXAMPLE 25

(5R,6S)-2-[2-(1-Methyltetrazol-5-ylthio)-ethyl]-6-(tert.-butyl-dimethyl-silyloxymethyl)-2-penem-3-carboxylic acid allyl ester Analogously to Example 4, 1.6 g of 2-[(3S,4R)-3-(tert.-butyl-dimethyl-silyloxymethyl)-4-[3-(1-methyltetrazol-5-ylthio)-propionylthio]-2-oxoazetidin-1-yl]-2-triphenylphosphoranylidenacetic acid allyl ester are converted into the title compound.

IR (methylene chloride): 5.62; 5.88; 6.22μ.

EXAMPLE 26

(5R,6S)-2-2-(1-Methyltetrazol-5-ylthio)-ethyl]-6-hydroxymethyl-2-penem-3-carboxylic acid allyl ester Analogously to Example 5, 0.71 g of (5R,6S)-2-[2-(1-methyltetrazol-5-ylthio)-ethyl]-6-(tert.-butyl-dimethyl-silyloxymethyl)-2-penem-3-carboxylic acid allyl ester is converted into the title compound.

IR (methylene chloride): 2.78; 5.62; 5.88; 6.35μ.

EXAMPLE 27

Sodium (5R,6S)-2-[2-(1-Methyltetrazol-5-ylthio)-ethyl]-6-hydroxymethyl-2-penem-3-carboxylate 0.265 g of (5R,6S)-2-[2-(1-methyltetrazol-5-ylthio)-ethyl]-6-hydroxymethyl-2-penem-3-carboxylic acid allyl ester are dissolved in 10 ml of absolute THF and cooled to −10°. After the addition of 15 mg of palladium tetrakis(triphenylphosphine) and 0.22 ml of tributyltin hydride the reaction mixture is stirred for a further 20 minutes at −10°. 0.047 ml of acetic acid is then added and the whole is then concentrated in a rotary evaporator. After partitioning the residue between water and ethyl acetate the pH of the aqueous phase is adjusted to 8.5 with aqueous $NaHCO_3$ solution. After concentration of the aqueous phase in a rotary evaporator, the substance is purified by chromatography over XAD-2 (eluant: water) UV (water $\lambda_{max}$: 305 nm.

EXAMPLE 28

(5R,6S)-2-[2-(1-Methyltetrazol-5-ylthio)-ethyl]-6-hydroxymethyl-2-penem-3-carboxylic acid 1-ethoxycarbonyloxyethyl ester 1.2 g of sodium iodide are dissolved in 3.7 ml of acetone, and 0.275 ml of ethyl-1-chloroethyl carbonate is added. The mixture is stirred for 3 hours at room temperature. The solution is then added dropwise to 15 ml of methylene chloride, and the precipitated inorganic salts are filtered off. The methylene chloride solution is concentrated to 2 ml and added, at 0°, to a solution of 0.365 g of (5R,6S)-2-[2-(1-methyltetrazol-5-ylthio)-ethyl]-6-hydroxymethyl-2-penem-3-carboxylic acid (sodium salt) in 4 ml of dimethylacetamide. The whole is then stirred for 3 hours at 0°, subsequently diluted with ethyl acetate and washed three times with water. The organic phases are dried over sodium sulphate and concentrated in a rotary evaporator. The crude product is purified over 10 g of silica gel with the eluant ethyl acetate. The title compound is obtained in the form of a white foam.

IR spectrum (methylene chloride): absorption bands at 5.59 and 5.75 μm.

EXAMPLE 29

(5R,6S)-2-[2-(1-Methyltetrazol-5-ylthio)-ethyl]-6-hydroxymethyl-2-penem-3-carboxylic acid pivaloyloxymethyl ester 0.6 g of sodium iodide is dissolved in 2 ml of acetone, and 0.15 ml of pivalic acid chloromethyl ester is added. The mixture is stirred at room temperature for 3 hours and then added dropwise to 7.5 ml of methylene chloride. The precipitated inorganic salts are filtered off. The methylene chloride solution is concentrated to 1 ml and added, at 0°, to a solution of 0.146 g of (5R,6S)-2-[2-(1-methyltetrazol-5-ylthio)-ethyl]-6-hydroxymethyl-2-penem-3-carboxylic acid (sodium salt) and 0.07 ml of diisopropylethylamine in 4 ml of N,N-dimethylacetamide. The whole is then stirred for 3 hours at 0°, subsequently diluted with ethyl acetate and washed three times with water. The organic phase is dried over sodium sulphate and concentrated in a rotary evaporator. The crude product is purified over 10 g of silica gel with the eluant ethyl acetate. The title compound is obtained in the form of a white foam.

IR spectrum (methylene chloride): absorption bands at 5.59 and 5.78 μm.

EXAMPLE 30

Dry ampoules or phials, each containing 0.5 g of sodium (5R,6S)-2-[3-(1-methyltetrazol-5-ylthio)-propyl]-6-hydroxymethyl-2-penem-3-carboxylate as active ingredient, are prepared as follows:

| Composition (for 1 ampoule or phial) | |
|---|---|
| active ingredient | 0.5 g |
| mannitol | 0.05 g |

A sterile aqueous solution of the active ingredient and the mannitol is subjected to freeze-drying under aseptic conditions in 5 ml ampoules or 5 ml phials, and the ampoules or phials are sealed and tested.

I claim:

1. 2-heterocyclylthio-lower alkyl-2-penem compounds of the formula

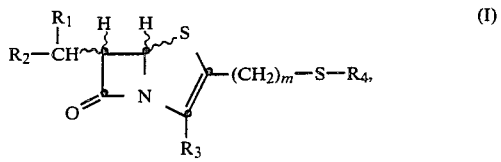

(I)

in which $R_1$ represents hydrogen or methyl; $R_2$ represents hydroxy; $R_3$ represents carboxy, lower alkanoyloxymethoxycarbonyl, or 1-lower alkoxycarbonyloxy-lower alkoxycarbonyl; $R_4$ represents a heterocyclic bonded to the sulfur atom via a ring carbon atom, said heterocyclic being selected from (a) 1,2,3-thiadiazol-4-yl, 1,2,3-thiadiazol-5-yl, 1,3,4-thiadiazol-2-yl or 1,2,4-thiadiazol-5-yl, each optionally substituted by lower alkyl, (b) 1,2,4-oxadiazol-5-yl or 1,3,4-oxadiazol-2-yl each optionally substituted by lower alkyl, (c) 1H- or 2H-tetrazol-5-yl optionally substituted by lower alkyl, carboxy-lower alkyl, sulpho-lower alkyl or by di-lower alkylamino-lower alkyl, and (d) pyridyl; and m represents 2 or 3, and pharmaceutically acceptable salts of such compounds of the formula I that have a salt-forming group, optical isomers of compounds of the formual I and mixtures of these optical isomers.

2. The compound of formula I according to claim 1 in which the penem ring is in the [5R, 6S] configuration.

3. Compounds of the formula I according to claim 1 in which $R_4$ represents 1,3,4-thiadiazol-2-yl, 2-methyl-1,3,4-thaidiazol-5-yl, 2-methyl-1,3,4-oxadiazol-5-yl, 1H-tetrazol-5-yl, 1-methyl-1H-tetrazol-5-yl, 1-carboxymethyl-1H-tetrazol-5-yl, 1-sulphomethyl-1H-tetrazol-5-yl, 1-(2-dimethylaminoethyl)-1H-tetrazol-5-yl, 2-methyl-2H-tetrazol-5-yl or 2-pyridyl.

4. (5R-6S)-configured compounds of the formula I according to claim 1 in which $R_1$ represents hydrogen, $R_2$ represents hydroxy, $R_3$ represents carboxy, $R_4$ represents 1H-tetrazol-5-yl substituted by lower alkyl or di-lower alkylamino-lower alkyl, and m is 2 or 3, and the pharmaceutically acceptable salts thereof.

5. (5R,6S)-2-[3-(1-methyl-1H-tetrazol-5-ylthio)-propyl]-6-hydroxymethyl-2-penem-3-carboxylic acid and pharmaceutically acceptable salts thereof according to claim 1.

6. (5R,6S)-2-[3-(1-dimethylaminoethyl-1H-tetrazol-5-ylthio)-propyl]-6-hydroxymethyl-2-penem-3-carboxylic acid and pharmaceutically acceptable salts thereof according to claim 1.

7. (5R,6S)-2-[2-(1-methyltetrazol-5-ylthio)-ethyl]-6-hydroxymethyl-2-penem-3-carboxylic acid and pharmaceutically acceptable salts thereof according to claim 1.

8. A pharmaceutical preparation containing an antibacterial therapeutically effective amount of a compound of the formula I according to claim 1 or a pharmaceutically acceptable salt thereof.

9. A method of treating bacterial infections in a mammal comprising administering to said mammal a therapeutically effective amount of a compound of the formula I according to claim 1 or of a pharmaceutically acceptable salt thereof.

* * * * *